US008939911B2

(12) United States Patent
Kosaku

(10) Patent No.: US 8,939,911 B2
(45) Date of Patent: Jan. 27, 2015

(54) ULTRASONIC PROBE AND APPARATUS FOR OBTAINING ULTRASONIC IMAGE

(75) Inventor: Hideki Kosaku, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1155 days.

(21) Appl. No.: 11/625,612

(22) Filed: Jan. 22, 2007

(65) Prior Publication Data

US 2007/0197914 A1    Aug. 23, 2007

(30) Foreign Application Priority Data

Jan. 25, 2006   (JP) .................................. 2006-016114
May 26, 2006   (JP) .................................. 2006-146228

(51) Int. Cl.
*A61B 8/14*    (2006.01)
*B06B 1/06*    (2006.01)
*A61B 8/08*    (2006.01)
*A61B 17/34*   (2006.01)
*A61B 8/00*    (2006.01)

(52) U.S. Cl.
CPC ............. *B06B 1/0622* (2013.01); *A61B 8/0841* (2013.01); *A61B 17/3403* (2013.01); *A61B 8/0833* (2013.01); *A61B 8/4455* (2013.01); *A61B 2017/3413* (2013.01)
USPC ........... 600/459; 600/443; 600/461; 606/181; 606/185; 310/334; 310/335; 310/336; 310/337

(58) Field of Classification Search
USPC .................. 600/437–472, 407; 606/181, 185; 310/334–337
See application file for complete search history.

(56) References Cited

U.S. PATENT DOCUMENTS 4,603,701 A * 8/1986 Chen ............................. 600/459
5,078,149 A * 1/1992 Katsumata et al. ........... 600/459
5,415,175 A * 5/1995 Hanafy et al. ................. 600/459

(Continued)

FOREIGN PATENT DOCUMENTS

CN    1626041 A    6/2005
JP    3-128048     5/1991

(Continued)

OTHER PUBLICATIONS

Machine Translation of WO2004/064643 published on Aug. 5, 2004.*

*Primary Examiner* — Unsu Jung
*Assistant Examiner* — Joseph M Santos Rodriguez
(74) *Attorney, Agent, or Firm* — Oblon, Spivak, McClelland, Maier & Neustadt, L.L.P.

(57) ABSTRACT

The ultrasonic probe comprises an ultrasonic transducer section in which a plural of ultrasonic transducers arranged in a row in the scanning direction, an acoustic lens and a low attenuation medium, and further comprises a probe shell housing the ultrasonic transducer section, acoustic lens, and low attenuation medium. In the probe shell, the low attenuation medium is located at the top end (contact surface with a subject to be examined) of the ultrasonic probe, and the low attenuation medium, acoustic lens, and ultrasonic transducer section are located in order. In this way, the ultrasonic waves transmitted from the ultrasonic transducer section are converged by the acoustic lens and transmitted outside the probe shell through the low attenuation medium. The reflection waves from the subject to be examined are received by the ultrasonic transducer section through the low attenuation medium.

23 Claims, 19 Drawing Sheets

(56) References Cited

U.S. PATENT DOCUMENTS

| | | | |
|---|---|---|---|
| 6,068,599 A * | 5/2000 | Saito et al. | 600/454 |
| 6,695,786 B2 * | 2/2004 | Wang et al. | 600/461 |
| 7,070,565 B2 * | 7/2006 | Vaezy et al. | 600/459 |
| 7,678,054 B2 * | 3/2010 | Okazaki et al. | 600/459 |
| 2003/0229331 A1 * | 12/2003 | Brisken et al. | 604/500 |
| 2005/0033177 A1 * | 2/2005 | Rogers et al. | 600/455 |
| 2005/0122004 A1 | 6/2005 | Shibamoto et al. | |

FOREIGN PATENT DOCUMENTS

| | | |
|---|---|---|
| JP | 8-10256 | 1/1996 |
| JP | 11-206764 | 8/1999 |
| JP | 2000-201929 | 7/2000 |
| JP | 2001-120550 | 5/2001 |
| WO | WO 2004064643 A1 * | 8/2004 |
| WO | WO 2005/057205 A1 | 6/2005 |

\* cited by examiner

PROBE SURFACE

TRANSMISSION
/RECEPTION
DIRECTION

SCANNING DIRECTION

TRANSMISSION
/RECEPTION
DIRECTION

SLICE DIRECTION

FIG.8
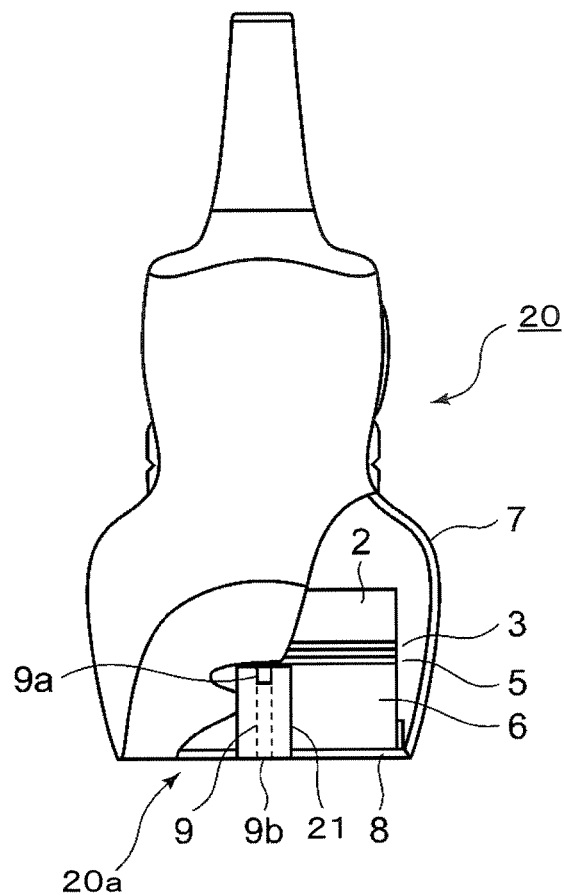
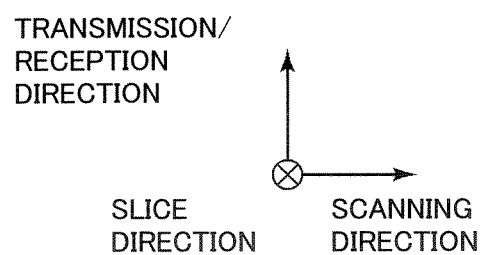

TRANSMISSION
/RECEPTION
DIRECTION

SLICE
DIRECTION

SCANNING
DIRECTION

ULTRASONIC PROBE AND APPARATUS FOR OBTAINING ULTRASONIC IMAGE

BACKGROUND OF THE INVENTION

1. Field of the Invention

The present invention relates to an ultrasonic probe for transmitting ultrasonic waves into a subject to be examined and receiving the reflection waves from the subject to be examined and an apparatus for obtaining an ultrasonic image comprising said ultrasonic probe for obtaining diagnostic information inside the subject to be examined.

2. Description of the Related Art

An apparatus for obtaining an ultrasonic image is known for producing an image inside a subject to be examined based on the reflection waves from the subject to be examined by scanning inside the subject to be examined with ultrasonic waves. Such an apparatus for obtaining an ultrasonic image transmits ultrasonic waves inside a subject to be examined by an ultrasonic probe with ultrasonic transducers, and receives the reflection waves generated by non-matching with the acoustic impedance in the subject to be examined.

The ultrasonic probe is provided with a plural of ultrasonic transducers arranged in the scanning direction. The ultrasonic transducers generate ultrasonic waves by oscillation based on the transmission signal and produce receiving signals by receiving the reflection waves. As explained, the transmission/reception of ultrasonic waves is done by ultrasonic transducers; however, the acoustic impedance of the ultrasonic transducer and that of the subject to be examined differs greatly. As a result of ultrasonic waves being directly transmitted into the subject to be examined, the reflection is excessively large. For this reason, an acoustically matching layer is installed between the ultrasonic waves and the subject to be examined to make the acoustic agreement favorable by changing the acoustic impedance gradually with the acoustic adjusting layer. In addition, the ultrasonic waves generated from flat ultrasonic transducers are transferred in the shape of a plain wave, resulting in the ultrasonic waves being dispersed naturally. For this, an acoustic lens is used to converge the ultrasonic waves at a focal point at a certain depth, as taught in Japanese Unexamined Patent Application 2000-201929 and Japanese Unexamined Patent Application H3-128048, the disclosure of which are hereby incorporated by reference.

Here the ultrasonic probe relating to the prior art is explained in reference to FIG. 1. FIG. 1 represents a perspective view showing the outline constitution of the head of the ultrasonic probe relating to the prior art. The ultrasonic probe consists of a head side and cable side, but only the head side is shown in FIG. 1.

As shown in FIG. 1, for the ultrasonic probe relating to the prior art, an ultrasonic transducer section 3 is installed on a backing material 2, and an acoustic matching layer 4 is installed on the ultrasonic transducer section 3. Here the acoustic matching layer 4 is constituted by a first acoustic matching layer 4*a* and a second acoustic matching layer 4*b*. In addition, an acoustic lens 5 is installed on the acoustic matching layer 4. Further, the ultrasonic transducer section 3 and acoustic matching layer 4 are multiply divided and configured in the scanning direction.

However, with the ultrasonic probe relating to the prior art having the above constitution, the ultrasonic waves are not sufficiently converged immediately after being transferred from the acoustic lens 5 to the subject to be examined, providing an unstable sound field. The image obtained based on the unstable sound field is unclear compared to an image in a region where ultrasonic waves are converged.

Here the sound field to be formed by the ultrasonic probe is explained in reference to FIG. 2A and FIG. 2B. FIG. 2A shows the sound field distribution of ultrasonic waves to be transmitted or received by the ultrasonic probe relating to the prior art. FIG. 2B shows the sound pressure at distance x from the surface of the ultrasonic probe relating to the prior art. At the same time, the sound field distribution shown in FIG. 2A and FIG. 2B is that formed by the ultrasonic transducer of a disk (diameter a), and is extracted from the handbook of ultrasonic wave equipment for medical application (Electric Industrial Association of Japan: EIAJ), the disclosure of which are hereby incorporated by reference.

FIG. 2A shows the sound field distribution of ultrasonic waves radiated from the surface of the ultrasonic probe relating to the prior art, in which the intensity of sound pressure is expressed by the shade of color. In FIG. 2A, the thicker portion indicates higher sound pressure and the thin portion lower sound pressure of ultrasonic waves.

An area in which the distance x from the surface of an ultrasonic probe is less than $D_1$ is referred to as a short distance sound field whereas an area exceeding the distance $D_1$ is referred to as a long distance sound field. The position of distance $D_1$ corresponds to the position of the focus of ultrasonic waves in the slice direction (direction perpendicular to the scanning direction). Namely, the position of distance $D_1$ corresponds to the position at which an ultrasonic wave beam is focused in the slice direction. The width of the beam pattern of ultrasonic waves relates to the resolution of ultrasonic wave images at which a narrower width provides higher resolution.

With the ultrasonic probe relating to the prior art, as shown in FIG. 2A, the sound field distribution near the surface of the ultrasonic probe (near the surface of acoustic lens 5) provides a sound field distribution in the stripes of complicated intensity. The ultrasonic wave image produced based on the signal obtained from the region with sound field distribution in such stripes does not provide a clear image. In the prior art, since the surface of the acoustic lens 5 forms a contact surface to a subject to be examined (living body), the sound pressure distribution near the subject to be examined (living body) is uneven, thus preventing a clear image from being obtained near the surface of the living body.

The sound field distribution shown in FIG. 2A and FIG. 2B is that formed by ultrasonic transducers of a disk shape, but ultrasonic transducers of a rectangular shape show similar characteristics as that shown in FIG. 2A and FIG. 2B, although the distribution shape differs to some extent.

The ultrasonic waves transmitted into a subject to be examined (living body) are attenuated inside the subject to be examined. Particularly in the case of reflection waves from a deep position, the attenuation is large, thus making the intensity of the reflection wave small. Therefore, in order to receive the reflection waves from a deeper spot while maintaining their intensity, the ultrasonic transducer is required to be large. However, the larger the ultrasonic transducer is, the larger the top end of the ultrasonic probe (contact surface with the subject to be examined) becomes, resulting in the lack of the operability. In order to upgrade the operability of ultrasonic probes, the contact surface to a living body must be reduced. For this purpose, the ultrasonic transducer should be minimized. Smaller ultrasonic transducers degrade the sensitivity, preventing a clear image from being obtained.

On the other hand, making the ultrasonic transducer causes thickness in the direction perpendicular to the scanning direction, resulting in receiving unnecessary reflection waves in that direction. This deteriorates the definition of the ultrasonic wave mage.

Also, a puncture method is popularly conducted by injecting puncture needles such as injection needles into a living body to sample tissues including tumors or local injection of medicine. Said puncture method is conducted by observing tomography image obtained by an ultrasonic wave image processing device in order to assure the correct puncturing of tissues such as target tumors.

In order to inject the abovementioned puncture needle into a living body, a puncture adapter is used. For the puncture adapter, an acoustic coupler to be mounted on the transmission/reception surface of an ultrasonic probe for use is known. The acoustic coupler for external mounting has a puncture needle guide to inject the puncture needle into a targeted spot, and the puncture needle is injected into a living body through the puncture needle guide, as taught in Japanese Unexamined Patent Application 2005-144028 and Japanese Examined Patent Application H1-17693, the disclosure of which are hereby incorporated by reference.

In addition, a method for injecting a puncture needle into a living body is known in which a notch on a part of an ultrasonic transducer and a puncture needle guide on the notch section are provided.

Injecting a puncture needle into a living body at around the center of the transmission/reception plane of an ultrasonic probe by using an acoustic coupler for external fitting or providing a notch on a part of an ultrasonic transducer allows the puncture needle to be depicted at around the center of a tomography image. In this way, a puncture needle is allowed to be injected into a living body while identifying the puncture needle from the near part of the body surface.

When the acoustic coupler for external mounting relating to the prior art is used, the puncture needle can be checked visually by a tomography image before injecting the puncture needle into a living body. However, in this case, the ultrasonic probe should be used under the state in which the acoustic coupler for external mounting is removed. Therefore, the driving condition of the ultrasonic probe should be set under the state when the acoustic coupler for external fitting is removed. This driving condition includes the driving voltage to be applied to the ultrasonic transducer, the focus position of ultrasonic waves, etc.

In the case of imaging with mounting the acoustic coupler for external mounting to the ultrasonic probe after the driving condition was set when the acoustic coupler for external fitting is removed, the driving condition may not be appropriate when the acoustic coupler for external fitting is mounted. For example, if the driving voltage of the focus position of ultrasonic waves is set to properly drive the ultrasonic probe when the acoustic coupler for external fitting is removed, there will be a problem of excessively low driving voltage or deviation in the focus position from a desired position with mounting the acoustic coupler for external mounting.

On the other hand, in the case of imaging with removing the acoustic coupler for external mounting from the ultrasonic probe under the state while setting the driving condition under the state when the acoustic coupler for external mounting is mounted, the driving condition may not be appropriate under the state when the acoustic coupler for external fitting is removed. For example, when setting the driving voltage or focus position of ultrasonic waves to properly drive the ultrasonic probe with the acoustic coupler for external mounting mounted, there may be a problem of excessively high driving voltage or deviation in the focus position from the desired position when the acoustic coupler for external mounting is removed.

As explained above, the ultrasonic waves have not been sufficiently converged immediately after being transferred from the acoustic lens outwardly, resulting in an unstable sound field. The ultrasonic wave image obtained from the unstable sound field will be unclear compared to the ultrasonic wave image in a region where ultrasonic waves have been converged. In the ultrasonic probe with the acoustic coupler removed, the sound field distribution near the body surface is not uniform as the surface of the acoustic lens is the contact surface with the living body, preventing a clear image from being obtained near the surface of a living body.

When a notch section is provided on a part of the ultrasonic transducer, which is a generating source of ultrasonic waves, there may be a problem of unstable luminance of the tomography image due to deteriorated sensitivity of the notch section.

SUMMARY OF THE INVENTION

The embodiments of the present invention are intended to provide an ultrasonic probe and an ultrasonic wave image processing device therewith by which a clear image near the surface of a living body is obtained.

In addition, the embodiments of the present invention are intended to provide an ultrasonic probe and an ultrasonic wave image processing device therewith, by which a clear image near the surface of a living body is obtained and by which a puncture needle by an ultrasonic wave image is identified before the puncture needle is injected into the surface of a living body.

An ultrasonic probe according to the first embodiment of the present invention comprises an ultrasonic transducer section which arranges a plural of ultrasonic transducers, a low attenuation medium, and a probe shell housing the low attenuation medium and the ultrasonic transducer section, wherein the ultrasonic transducer section transmits ultrasonic waves to said subject to be examined through the low attenuation medium and receives the reflection waves from the subject to be examined.

According to the first embodiment, the transmission of ultrasonic waves through the low attenuation medium housed inside the probe shell allows a uniform and stable sound field distribution to be obtained even near the contact surface with the subject to be examined. This enables a clear image to be obtained near the contact surface with the subject to be examined.

Further, according to the first embodiment, installation of a low attenuation medium allows the temperature of the contact surface with a living body to be lowered. This enables ultrasonic waves to be transmitted at a higher output than that of the ultrasonic probe relating to the prior art.

Moreover, an ultrasonic probe according to the second embodiment of the present invention comprises an ultrasonic probe according to the first embodiment, wherein a puncture needle guide for guiding the puncture needle into the subject to be examined is provided in the low attenuation medium.

According to the second embodiment, a clear image near the contact surface to a subject to be examined is obtained since a uniform and stable sound field distribution are obtained near the contact surface to a subject to be examined in the same manner as the first embodiment.

Further, according to the second embodiment, the transmission of ultrasonic waves through the low attenuation medium allows the puncture needle guided inside the low attenuation medium to be depicted as an ultrasonic wave image. This enables the puncture needle to be identified as an ultrasonic wave image from a stage before injecting the puncture needle into the surface of a body.

An ultrasonic wave image processing device according to the third embodiment of the present invention comprises: an ultrasonic transducer section which arranges a plural of ultrasonic transducers, transmits ultrasonic waves to a subject to be examined and receives the reflection waves from the subject to be examined, a low attenuation medium, and a probe shell housing the low attenuation medium and the ultrasonic transducer section wherein the ultrasonic transducer section comprises: an ultrasonic probe which transmits ultrasonic waves to the subject to be examined through the low attenuation medium and receives the reflection wave from the subject to be examined; a transmission/reception section which has the ultrasonic probe transmit ultrasonic waves and receives the reflection waves received by the ultrasonic probe; and an image data producing section at which ultrasonic wave image data is produced based on the output from the transmission/reception section.

The fourth embodiment of the present invention comprises an apparatus for obtaining an ultrasonic image according to the third embodiment, wherein a puncture needle guide to guide the puncture needle into a subject to be examined is installed on the low attenuation medium.

An ultrasonic probe according to the fifth embodiment of the present invention comprises: an ultrasonic transducer section with ultrasonic transducers installed in a row in the scanning direction that transmits ultrasonic waves to a subject to be examined and receives the reflection waves from said subject to be examined, a convergence component for converging the ultrasonic waves to be transmitted and received in the slice direction perpendicular to said scanning direction; a low attenuation medium in solid state formed such that it is tapered toward the contact surface side of said subject to be examined; and a probe shell housing said low attenuation medium, said convergence component and said ultrasonic transducer section in order, said low attenuation medium locating at the contact surface side of said subject to be examined, wherein; said ultrasonic transducer section transmits ultrasonic wave to said subject to be examined and receives the reflection waves from said subject to be examined through said low attenuation medium, and the position of the top end of the contact surface side to said subject to be examined substantially equal the position of the focus of ultrasonic wave.

An ultrasonic probe according to the sixth embodiment of the present invention comprises an ultrasonic probe according to the fifth embodiment, wherein a puncture needle guide is installed on the low attenuation medium to guide the puncture needle into a subject to be examined by locating the puncture needle horizontally to the transmission direction and scanning direction

BRIEF DESCRIPTION OF THE DRAWINGS

FIG. 6 B represents a side view showing the outline constitution of the head side of the ultrasonic probe according to the second embodiment of the present invention.

FIG. 8 represents a front view showing the outline constitution of the head side of the ultrasonic probe according to the third embodiment of the present invention.

DETAILED DESCRIPTION OF THE EMBODIMENTS

[Embodiment 1]

The ultrasonic probe according to Embodiment 1 of the present invention is explained in reference to FIG. 3A, FIG. 3B, FIG. 4 and FIG. 5. In Embodiment 1, an explanation is provided for a so-called one-dimensional ultrasonic probe, which installs a plural of ultrasonic transducers in a row.

Figure 3:
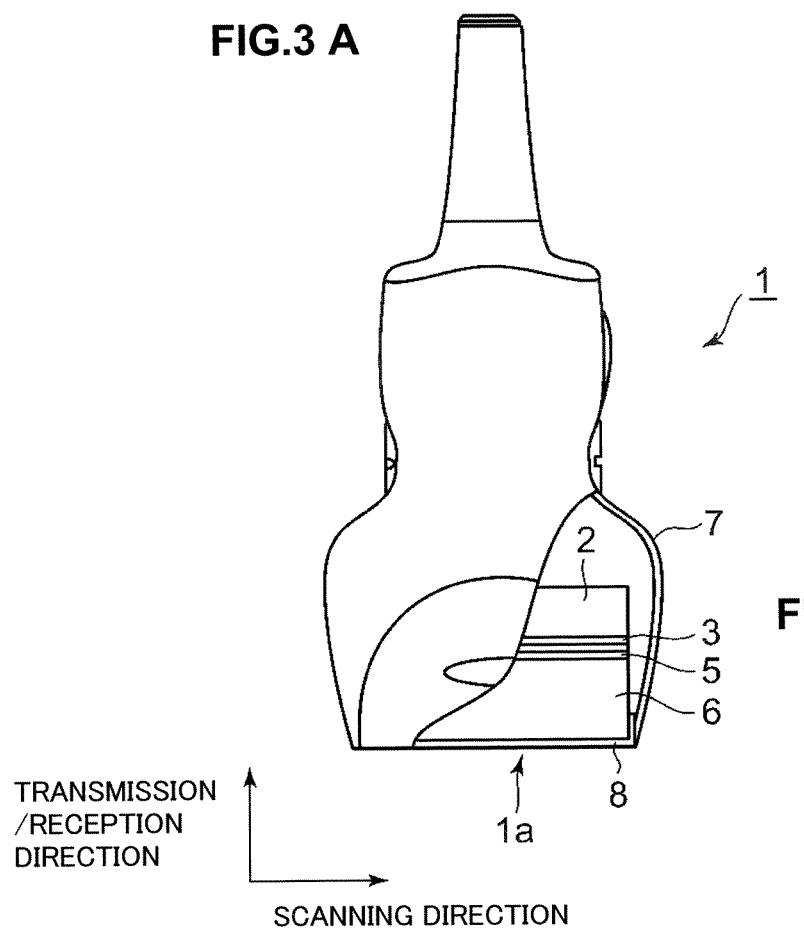
FIG. 3A represents a front view showing the outline constitution of the head side of the ultrasonic probe according to the first embodiment of the present invention.
FIG. 3B represents a side view showing the outline constitution of the head side of the ultrasonic probe according to the first embodiment of the present invention.
Figure 3:
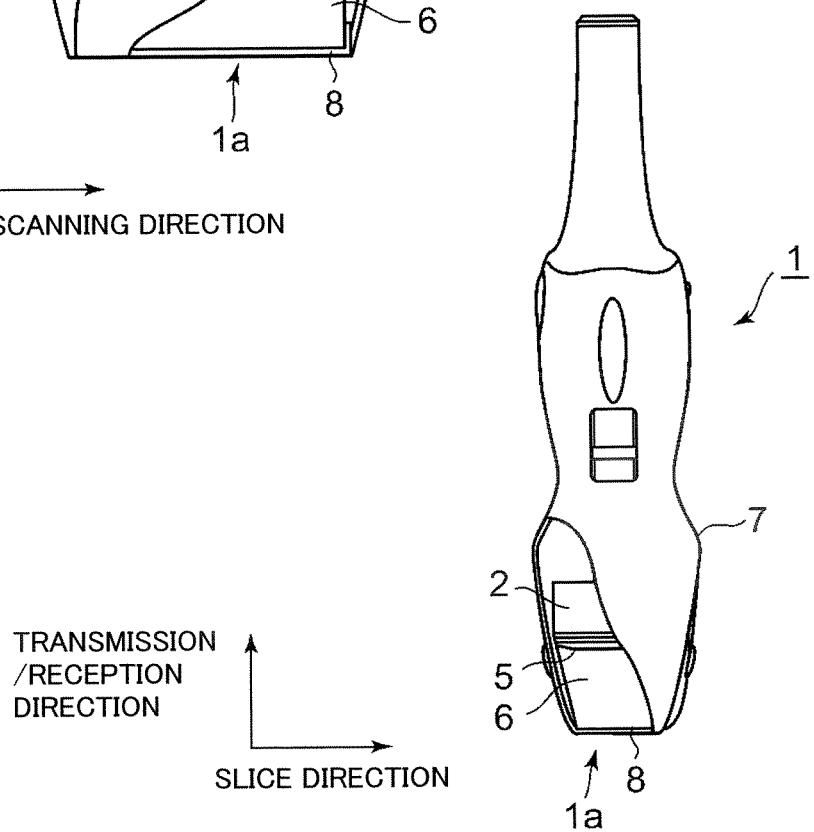
Figure 4:
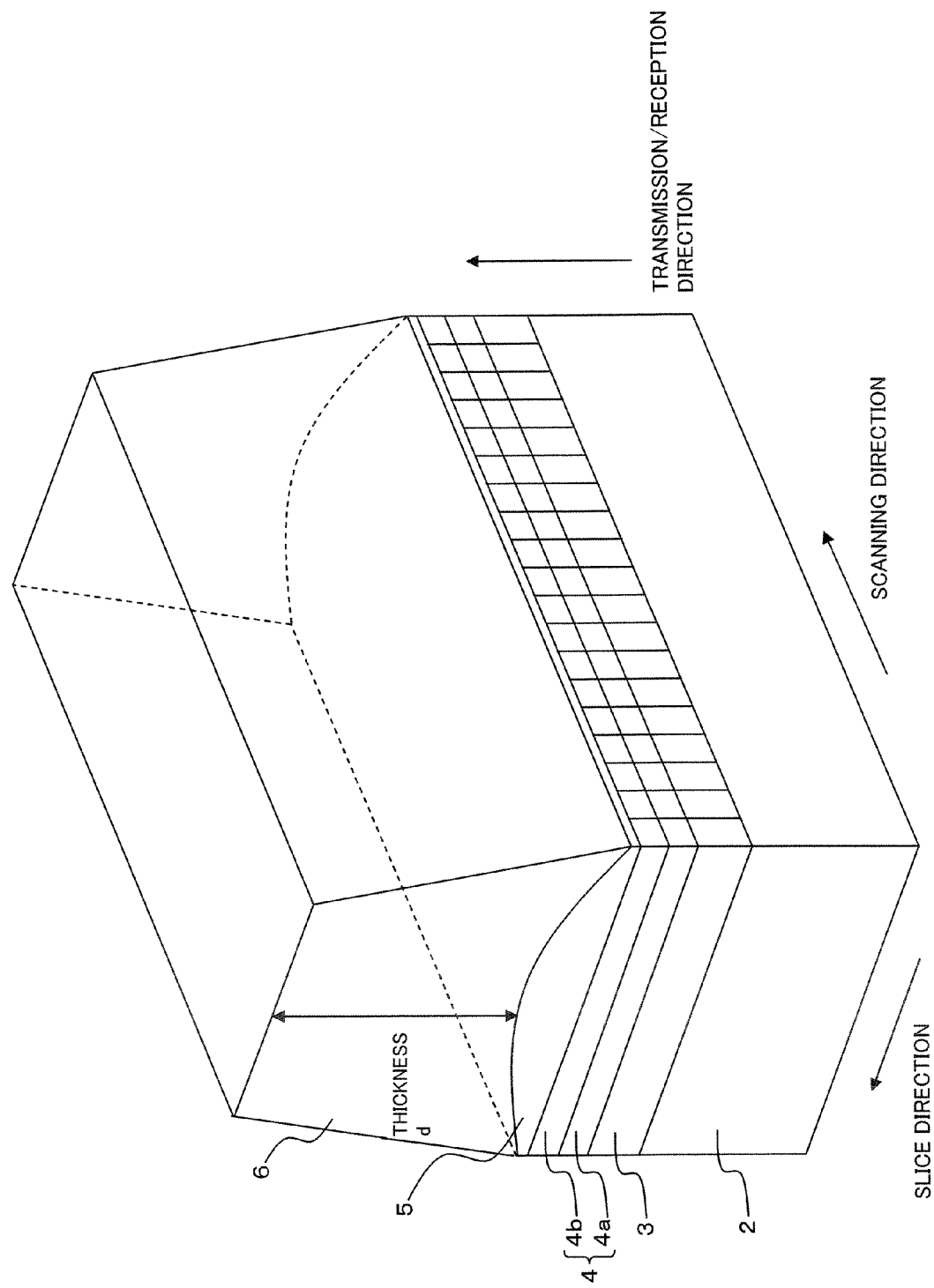
FIG. 4 represents a perspective view showing the outline constitution of the head side of the ultrasonic probe according to the first embodiment of the present invention.

The constitution of the ultrasonic probe according to Embodiment 1 of the present invention is explained in reference to FIG. 3A, FIG. 3B and FIG. 4. FIG. 3A represents a front view of the outline constitution of the head side of the ultrasonic probe according to Embodiment 1 of the present invention. FIG. 3B represents a side view showing the outline constitution of the head side of the ultrasonic probe according to the embodiment of the present invention. FIG. 3A indicates the ultrasonic probe 1 viewed from the slice direction (direction perpendicular to the scanning direction). FIG. 3B indicates the ultrasonic probe 1 viewed from the scanning direction. In a part of FIG. 3A and FIG. 3B, each of built-in sections is shown. FIG. 4 represents a perspective view showing the outline constitution of the head side of the ultrasonic probe according to Embodiment 1 of the present invention. FIG. 3A, FIG. 3B and FIG. 4 show the head side of the ultrasonic probe.

As shown in FIG. 3A, FIG. 3B and FIG. 4, the ultrasonic probe 1 provides an ultrasonic transducer section 3 on a backing material 2, and an acoustic matching layer 4 on the ultrasonic transducer section 3. Further, an acoustic lens 5 is installed on the acoustic matching layer 4. Also, the ultrasonic transducer section 3 and the acoustic matching layer 4 are multiply divided and arranged. Moreover, at the ultrasonic probe 1 according to Embodiment 1, a low attenuation medium 6 is installed on the acoustic lens 5.

The backing material 2 is provided for attenuating and absorbing an ultrasonic wave component, which is not necessary for image extraction of the ultrasonic wave image processing device among the ultrasonic wave oscillations oscillated by the ultrasonic transducer section 3 or those at receiving. For the backing material 2, ferrite rubber, epoxy resin or urethane rubber mixed with micro balloon is usually used.

The ultrasonic transducer section 3 provides a plural of ultrasonic transducers which are divided and installed in a row. Installing a plural of ultrasonic transducers in a row in the scanning direction forms a one-dimensional ultrasonic probe. The ultrasonic transducer section 3 consists of, for example, ceramic materials such as lead zirconium titanate $Pb(Zr,Ti)O_3$, niobate lithium ($LiNbO_3$), titanic acid barium ($BaTiO_3$), or titanic acid lead ($PbTiO_3$). In addition, electrodes (not shown in the figure) are installed on the upper and lower surfaces of the ultrasonic transducer section 3.

For the acoustic matching layer 4, epoxy resin or plastic materials are used. The acoustic matching layer 4 is installed to upgrade the acoustic matching of the acoustic impedance of the ultrasonic transducer section 3 and that of the subject to be examined. The acoustic matching layer 4 may be employed for one, two or more layers. In the ultrasonic probe 1 of Embodiment 1, two layers of the acoustic matching layer are employed. In this case, the acoustic impedance of the second acoustic matching layer 4b is designed to be smaller than that of the first acoustic matching layer 4a. By making the acoustic matching layers in a plural of layers such that they gradually match the acoustic impedance, signal loss due to the difference in the acoustic impedance caused by the direct connection of the body surface of the subject to be examined and the ultrasonic transducer section 3 is suppressed.

The acoustic lens 5, as one example of the convergence component, intermediates the transmission/reception of ultrasonic waves by the ultrasonic transducer section 3. By this acoustic lens, the ultrasonic wave forms an acoustic focus in the direction of the slicing (perpendicular to the scanning direction) at a specified depth in a subject to be examined. In addition, the acoustic focus of ultrasonic waves in the scanning direction is formed by switching the timing of the transmission and reception of a plural of ultrasonic transducers. The shape of the acoustic lens 5 shown in FIG. 3A, FIG. 3B and FIG. 4 is just an example and is not limited to this shape. Any shape can be employed as long as it can converge ultrasonic waves in the slice direction.

Also, as shown in FIG. 3A and FIG. 3B, a backing material 2, an ultrasonic transducer section 3, an acoustic matching layer 4, an acoustic lens 5, and a low attenuation medium 6 are housed inside a probe shell 7 (case). The low attenuation medium 6 is housed in the probe shell 7 so that it is installed at the top end 1a side of the ultrasonic probe 1, namely at the contact surface with a subject to be examined.

By forming the constitution as above, the ultrasonic waves transmitted from the ultrasonic transducer section 3 are converged in the slice direction (perpendicular to the scanning direction) by the acoustic lens 5, and are applied to the external part of the ultrasonic probe 1 through the low attenuation medium 6. Further, the reflection waves from the subject to be examined incident inside the ultrasonic probe 1 and are then received at the ultrasonic transducer section 3 through the acoustic lens 5.

Here, the shape of the low attenuation medium 6 is explained. As shown in the FIG. 4 perspective view, the surface (contacting the low attenuation medium 6) of the acoustic lens 5 has a curved convex configuration. The surface of the low attenuation medium 6 contacting with the acoustic lens 5 (sometimes referred to as "the first surface") is formed in a concave surface to couple with the convex surface of the acoustic lens 5. Also, the low attenuation medium 6 is formed to taper toward the top, with its width formed in the direction of slicing of the low attenuation medium 6 such that it gradually narrows in the direction away from the acoustic lens 5 (transmission/reception direction). In other words, the sectional area perpendicular to the transmission/reception direction at the low attenuation medium 6 is formed such that the area is gradually reduced toward the direction leaving the acoustic lens 5 (transmission/reception direction). Further, it is formed to minimize the area of the surface opposed to the first surface (the surface at the top end 1a side of the ultrasonic probe 1, hereinafter referred as "the second surface").

In addition, the thickness of the low attenuation medium 6 in the transmission/reception direction is preferably determined based on the characteristics of the sound field distribution of the ultrasonic transducer section 3. For example, the sound field distribution of ultrasonic waves transmitted from the ultrasonic transducer of rectangular shape shows the same characteristics shown in FIG. 2A and FIG. 2B. Under these circumstances, just for the sake of convenience, the thickness of the low attenuation medium 6 is explained in reference to the sound field distribution shown in FIG. 2A and FIG. 2B. Here, the thickness indicates that in the transmission/reception direction of the low attenuation medium 6, with the thickness at the center in the slice direction referred to as "thickness d."

For example, the thickness of the low attenuation medium 6 is preferably determined such that the position of the top end 1a (contacting a subject to be examined) substantially agrees with the focus position of ultrasonic waves. Practically speaking, the thickness d of the low attenuation medium 6 is preferably greater than the distance $D_2$ as shown in FIG. 2B, and less than the distance $D_1$.

Figure 1:
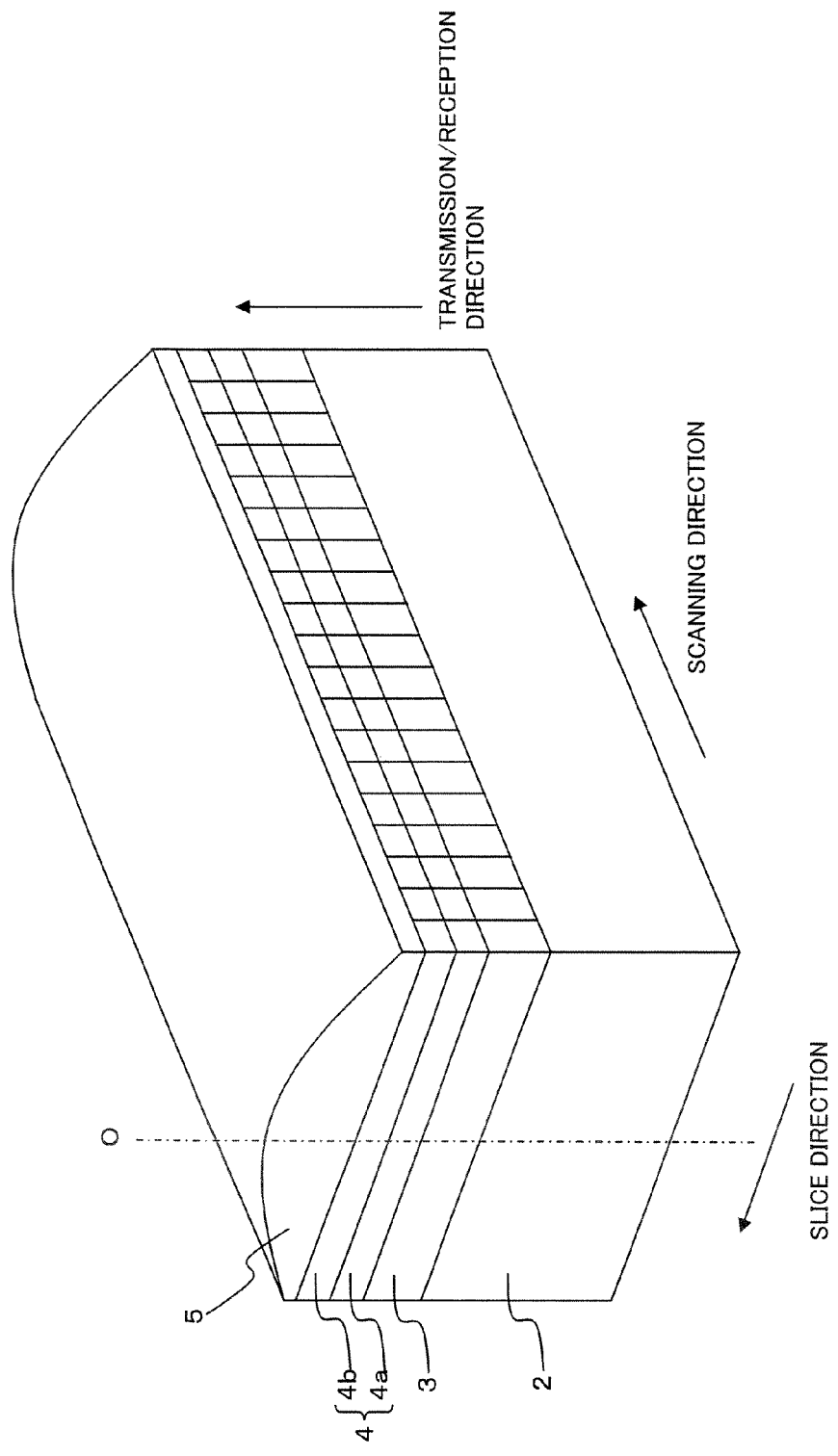
FIG. 1 represents a perspective view showing the outline constitution of the head side of the ultrasonic probe according to prior art.
Figure 2:
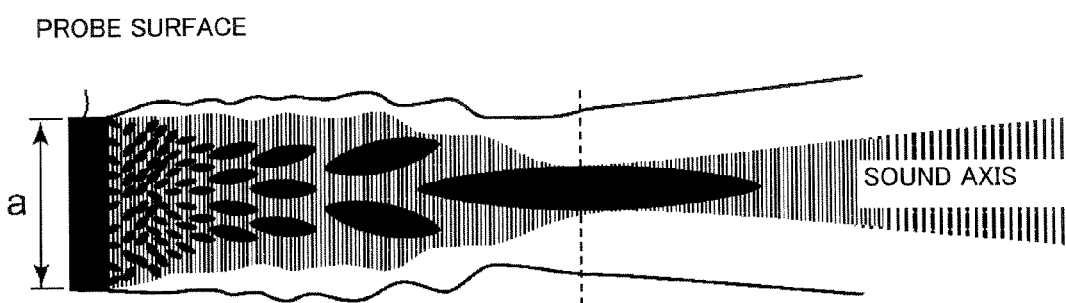
FIG. 2A indicates the sound field distribution of ultrasonic waves radiated from the surface of the ultrasonic probe according to prior art.
FIG. 2B represents a graph showing the sound pressure of ultrasonic waves at a position of distance x from the surface of the ultrasonic probe according to prior art.
Figure 2:
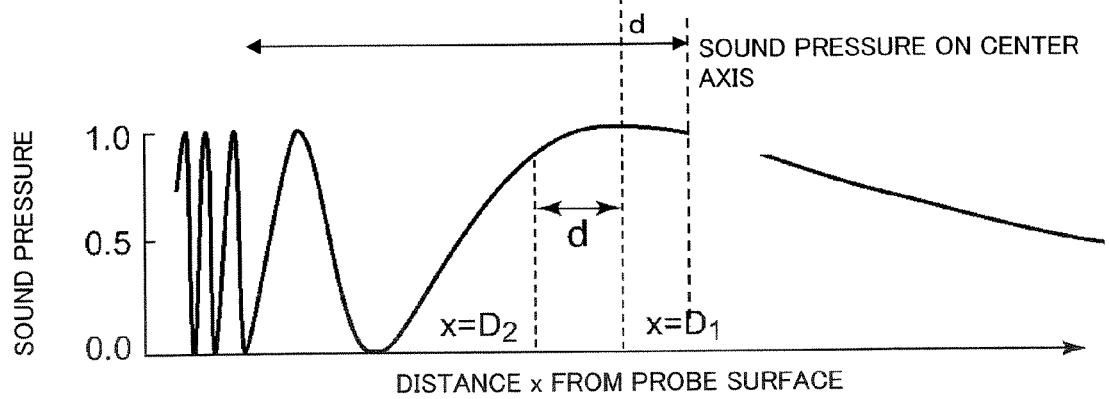

In the case of the ultrasonic probe according to the prior art without a low attenuation medium 6 installed, the sound field is stable when the distance x from the surface of the ultrasonic probe is greater than the distance $D_2$ as shown in FIG. 2B. Therefore, making the thickness d of the low attenuation medium 6 installed on the acoustic lens 5 greater than $D_2$ allows the distance from the surface of the acoustic lens 5 to the top end 1a to be made greater than the distance $D_2$. By doing so, the sound field distribution near the top end 1a of the ultrasonic probe 1 can be a stable sound field distribution formed with a distance greater than $D_2$ shown in FIG. 2B. By installing the low attenuation medium 6 on the acoustic lens 5 as explained, and by transmitting ultrasonic waves through the low attenuation medium 6, a stable and uniform sound field distribution can be formed near the top end 1a (contacting subject to be examined), allowing a uniform sound field to be formed near the surface of the subject to be examined and thus obtaining a clear image of the surface of a living body.

Regarding the distance $D_2$ from the surface of the ultrasonic probe, a general definition is not easy because of the characteristics required for the ultrasonic probe 1, along with the shape or dimensions of the ultrasonic transducer. However, it is preferable to define it as the distance to the position where the sound field distribution of ultrasonic waves to be transmitted is situated.

In the case of the ultrasonic probe according to the prior art in which a low attenuation medium 6 is not installed, as shown in FIG. 2A and FIG. 2B, the spot near the distance $D_1$ corresponds to the focus position of ultrasonic waves in the slice direction (perpendicular to the scanning direction). Namely, the spot near the distance $D_1$ is the position where the ultrasonic wave beam is focused in the direction of slicing.

Consequently, making the thickness d of the low attenuation medium 6 less than the distance $D_1$ allows the focus position in the slice direction of ultrasonic wave to be formed at the external section of the ultrasonic probe 1. This allows the focus position in the slice direction of ultrasonic waves to be formed inside the subject to be examined, enabling a clear image inside the subject to be examined to be obtained.

As shown in FIG. 3A and FIG. 3B, a thin protective film 8 may be used to cover the top end 1a (contacting subject to be examined) of the ultrasonic probe 1. This protective film 8 is installed to secure the safety of the subject to be examined and the durability of the low attenuation medium 6.

Next, the material of the low attenuation medium 6 is explained. For the low attenuation medium 6, material having low attenuation of ultrasonic waves is used. Further, it is preferable that material with acoustic impedance similar to that of the subject to be examined (living body) be used. For this purpose, resin is used for the low attenuation medium 6, and more practically, butadiene rubber, a mixture of butadiene rubber and silicone (Japan Unexamined Patent Application H-8-615, the disclosure of which are hereby incorporated by reference), and a mixture of butadiene rubber and zinc oxide are used. Since the acoustic impedance of a subject to be examined (living body) counts for about 1.5 [Mrayl], use of resin with an acoustic impedance of 1.4~1.6 [Mrayl] for the low attenuation medium 6 enables better acoustic matching with the subject to be examined (living body) to be obtained.

Moreover, by adjusting the content of silicone or zinc oxide contained in the above mixtures, the characteristics (acoustic impedance or attenuation amount of ultrasonic waves) of the low attenuation medium 6 can be adjusted. Since the attenuation amount of ultrasonic waves changes depending on the ratio of mixtures, it is necessary to adjust the ratio of mixtures to meet the attenuation amount or the difference in the acoustic impedance at the position for diagnosis.

Further, the ratio of attenuation of ultrasonic waves by the low attenuation medium 6 is preferably less than 0.2 [dB/mm/MHz]. When the attenuation amount of ultrasonic waves exceeds 0.2 [dB/mm/MHz], the definition of the ultrasonic wave image to be obtained may deteriorate. While the attenuation of ultrasonic waves is preferably as low as possible, the ratio of the attenuation of ultrasonic waves can be reduced below 0.05 [dB/mm/MHz] by adjusting the ratio of mixtures. As explained, adjusting the ratio of mixtures of the low attenuation medium 6 can reduce the attenuation amount of ultrasonic waves; however, this causes a big difference between the acoustic impedance of the low attenuation medium 6 and the acoustic impedance of the living body (=about 1.5 [Mrayl]), possibly increasing the reflection between the acoustic lens and subject to be examined (living body). Therefore, it is preferable to determine the ratio of the mixing of the low attenuation medium 6 by considering the acoustic impedance in the relating region.

(Action)

Figure 5:
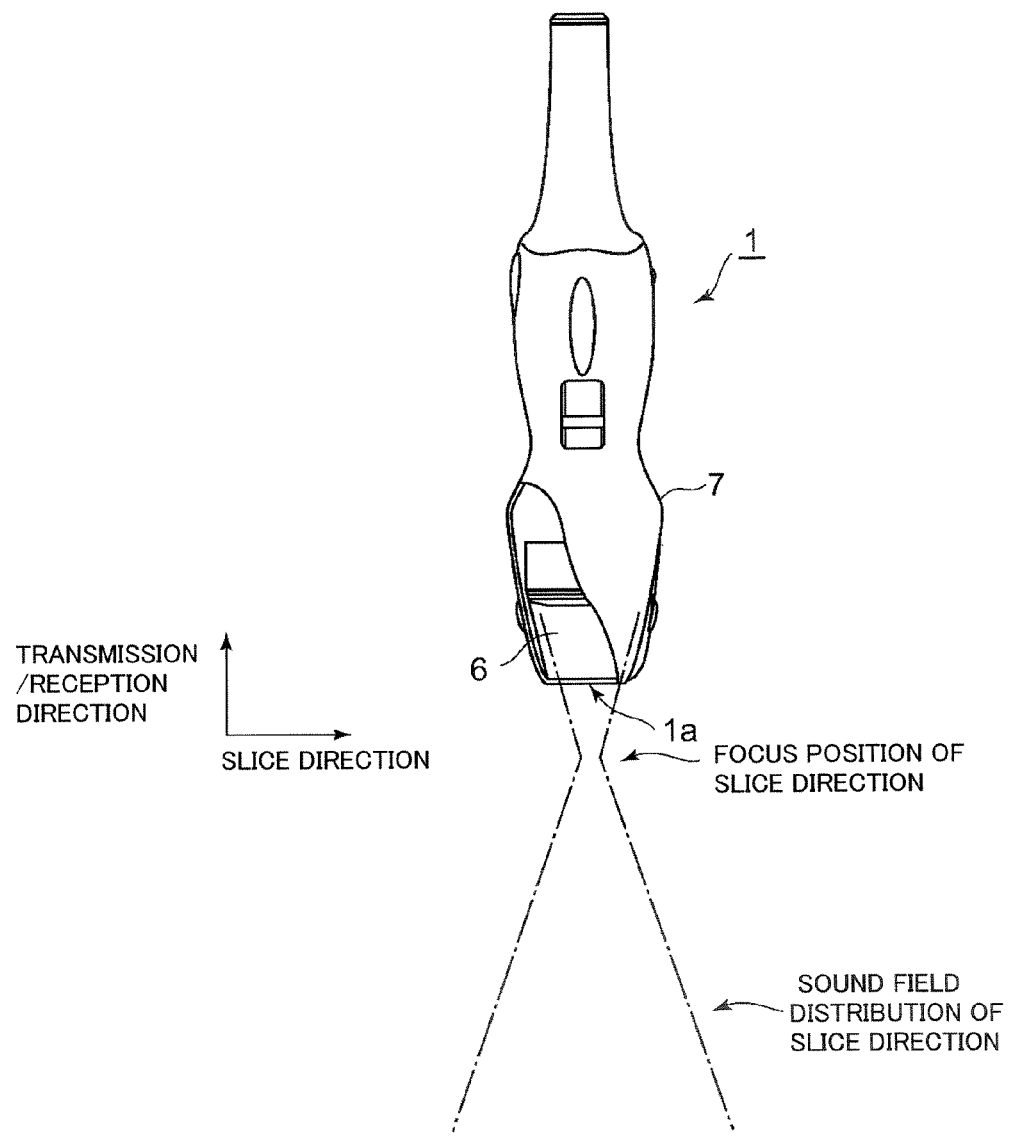
FIG. 5 indicates the sound field distribution of ultrasonic waves to be transmitted or received by the ultrasonic probe according to the first embodiment of the present invention, and viewed from the scanning direction.

According to the ultrasonic probe 1 with the above constitution, the following preferred action and effect can be obtained. The action and effect of the ultrasonic probe 1 according to Embodiment 1 are explained in reference to FIG. 3A, FIG. 3B, FIG. 4 and FIG. 5. FIG. 5 shows the sound field distribution of the ultrasonic waves to be transmitted or received by the ultrasonic probe according to Embodiment 1 of the present invention, in which the ultrasonic probe is viewed from the scanning direction. In a part of FIG. 5, each of built-in sections is shown.

According to the ultrasonic probe 1 relating to Embodiment 1, (1) a clear image can be obtained near the surface of a living body. (2) The area of the top end 1a (contacting the subject to be examined) of the ultrasonic probe 1 can be reduced, resulting in the upgrading the operability of the ultrasonic probe 1. (3) The sensitivity of the ultrasonic probe 1 can be increased. (4) Ultrasonic waves containing higher harmonics (harmonic frequency component) can be received even from a spot near the surface of a living body, enabling a high definition image with high resolution near the surface of a living body to be obtained. (5) When equaling the transmission output level to that of the ultrasonic probe according to the prior art, the temperature of the top end 1a of the ultrasonic probe 1 can be lowered compared to that of the prior art. As a result, the transmission output level of ultrasonic waves can be raised while keeping the temperature at the contact surface with a subject to be examined below or equal to the temperature of the contact surface of the ultrasonic probe according to the prior art. In this way, ultrasonic waves can be transmitted to a deeper spot of a subject to be examined (living body). The action and effects of (1) to (5) above are explained below.

First, effect (1) allowing a clear image near the surface of a living body to be obtained is explained. Since the distance from the acoustic lens 5 to the top end 1a of the ultrasonic probe 1 is extended by installing a low attenuation medium 6 on the acoustic lens 5, a stable and uniform sound field can be formed even at the top end 1a of the ultrasonic probe 1. For this reason, a stable and uniform sound field can be formed even at the surface of a subject to be examined (living body), thus enabling a clear image to be obtained even at the surface of a subject to be examined (living body).

For example, setting the thickness d of the low attenuation medium 6 to a length exceeding $D_2$ shown in FIG. 2B allows the sound field distribution at the top end 1a (contact surface with subject to be examined) of the ultrasonic probe 1 to be of a uniform and stable sound field distribution. As a result, a uniform and stable sound field can be formed near the surface of a living body, thus obtaining a clear image even at the surface of a subject to be examined (living body). Further, by setting the thickness d of the low attenuation medium 6 to a length less than $D_1$ shown in FIG. 2B, the focus position in the slice direction of ultrasonic waves, as shown in the side view of FIG. 5, can be formed outside of the ultrasonic probe 1. This allows the focus position of ultrasonic waves inside a subject to be examined (living body) to be formed to obtain a clear image inside the subject to be examined (living body).

Next, effect (2) which enables the contact surface with living body to be reduced is explained. According to the ultrasonic probe 1, the area of the top end 1a (contact surface with a subject to be examined) of the ultrasonic probe 1 can be shrunk. As shown in the side view of FIG. 5, the ultrasonic wave transmitted from the ultrasonic transducer section 3 is converged by the acoustic lens 5. Then, by installing the low attenuation medium 6 onto the acoustic lens 5, the distance from the surface of the acoustic lens 5 to the top end 1a of ultrasonic probe 1 can be extended by the thickness d of the low attenuation medium 6. As the ultrasonic wave can be focused when passing through the low attenuation medium, the ultrasonic wave being focused corresponding to the thickness d of the low attenuation medium 6 can be radiated externally from the top end 1a of ultrasonic probe 1. Namely, the ultrasonic wave beam passing through the low attenuation medium 6 is more focused than the ultrasonic wave immediately after passing through the acoustic lens 5. For this reason, the passing width of ultrasonic wave at the top end 1a (contact surface with a subject to be examined) of the ultrasonic probe 1 can be narrowed compared to the ultrasonic probe according to the prior art, making the surface of the acoustic lens 5 the contact surface with the subject to be examined. In other words, the area of the top end (contact surface with a subject to be examined) of the ultrasonic probe 1 is smaller than that of the ultrasonic probe according to the prior art. The top end 1a of the ultrasonic probe 1 thus shrunk allows the operability of the ultrasonic probe 1 to be upgraded.

Next, effect (3) to increase the sensitivity is explained. As explained in (2) above, as the area of the top end 1a (contact surface with subject to be examined) of the ultrasonic probe 1 can be reduced, e.g. when making the area of the top end 1a the same as that according to the prior art, the ultrasonic transducer section 3 can be enlarged compared to that of the prior art. Namely, even when the ultrasonic transducer section 3 is enlarged, installing the low attenuation medium 6 onto the acoustic lens 5 allows ultrasonic wave at the top end 1a of the ultrasonic probe 1 to be focused corresponding to the length of the low attenuation medium 6, thus eliminating the need to enlarge the top end 1a. On the other hand, according to the prior art, the acoustic lens 5 works as the contact surface with a subject to be examined, and as the ultrasonic waves are not sufficiently focused, the top end of the ultrasonic probe must be enlarged corresponding to the enlarged size of the ultrasonic transducer section 3.

According to the ultrasonic probe 1 as explained above, even when the ultrasonic transducer section 3 is enlarged, the top end 1a (contact surface with a subject to be examined) can be shrunk. Therefore, when making the size of the top end 1a equal to that of the ultrasonic probe according to the prior art, the ultrasonic transducer section 3 can be made larger than what is conventionally used. As a result, the sensitivity of the ultrasonic probe 1 can be increased without changing the size of the top end 1a of the ultrasonic probe 1, thus enabling more clear images to be formed.

Next, effect (4) regarding a higher harmonics component (harmonic frequency component) is explained. A method exists for obtaining highly precise images with high resolution by receiving ultrasonic waves having a higher harmonics component (harmonic imaging method). Conventionally, as the surface of the acoustic lens 5 is set as the top end (contact surface with a subject to be examined) of the ultrasonic probe, the distance from the ultrasonic transducer section 3 to the surface of a subject to be examined (living body) is short, preventing a sufficiently non-linear effect from being obtained near the surface of a living body. For this reason, a highly precise image with high resolution could not be obtained near the surface of a living body.

According to the ultrasonic probe 1 relating to Embodiment 1, as the low attenuation medium 6 is installed on the acoustic lens 5, the distance from the ultrasonic transducer section 3 to the surface of a subject to be examined (living body) is long. As a result, a sufficiently non-linear effect can be obtained near the surface of a living body, enabling an ultrasonic wave containing higher harmonics component (harmonic frequency component) to be obtained from even near the surface of a living body.

Next, effect (5) regarding the temperature of the contact surface with a living body and transmission output level of ultrasonic waves is explained. As the use of resin for the low attenuation medium 6, for example, lowers the heat transfer ratio of the low attenuation medium 6, heat generated in the ultrasonic transducer section 3 is difficult to transfer to a subject to be examined (living body) if the low attenuation medium 6 is installed onto the acoustic lens 5. Accordingly, if the transmission output level of ultrasonic waves is same compared to the ultrasonic probe according to the prior art, the temperature of the top end 1a of the ultrasonic probe 1 can be kept low. Compared to the prior art, as a result, the transmission output level of ultrasonic waves can be set to a higher level for the ultrasonic probe 1 according to Embodiment 1. Namely, if the transmission output level of ultrasonic waves is higher compared to the prior art, the temperature of the top end 1a of the ultrasonic probe 1 can be kept lower or at the same temperature. As the setting of the transmission output of ultrasonic waves is higher than the prior art, ultrasonic waves can be transmitted more deeply inside the subject to be examined (living body), thus enabling the range of observation to be widened.

Further, an item to be considered when designing an ultrasonic probe is the temperature of the top end 1a (contact surface with a subject to be examined) of the ultrasonic probe. The ultrasonic probe should be designed such that the temperature of the contact surface with a subject to be examined being applied to the transmission/reception of ultrasonic waves stays within the temperature range defined by the standard (IEC-60601-2-37). Namely, the transmission output level of ultrasonic waves must be set such that it stays within the temperature range defined by the standard (EC-60601-2-37).

In the case of the ultrasonic probe according to the prior art, as the surface of the acoustic lens 5 is the contact surface with a subject to be examined, the transmission output level is required to be set such that the temperature of the acoustic lens 5 stays within the range of the temperature defined by the above standard.

In the case of the ultrasonic probe 1 according to Embodiment 1, in which the low attenuation medium 6 is installed on the acoustic lens 5, the transmission output level of ultrasonic wave may be set such that the temperature of the top end 1a stays within the temperature range defined by the above standard.

As described above, if the transmission output level of ultrasonic waves is same, the temperature of the top end 1a (contact surface with subject to be examined) of the ultrasonic probe 1 according to Embodiment 1 stays lower than the temperature of the top end of the ultrasonic probe according to the prior art. According to the ultrasonic probe 1, as the temperature of the top end 1a can be lower than the prior art when transmitted ultrasonic waves are at the same transmission output level, the transmission output level of ultrasonic waves can be set to a higher level than the ultrasonic probe according to the prior art. Namely, according to the ultrasonic probe 1 related to Embodiment 1, if the transmission output of ultrasonic waves is set to a high level, the temperature of the top end 1a does not significantly rise, allowing the top end 1a to be kept within the temperature range defined by the above standard.

Following the standard (IEC60601-2-37), the temperature of the contact surface with a subject to be examined should be arranged so as not to exceed the specified temperature. According to the ultrasonic probe 1 related to Embodiment 1, the temperature of the contact surface with the subject to be examined can be kept within the range of the above standard, if the transmission output level of ultrasonic waves is raised so as to exceed the ultrasonic probe relating to the prior art. In Embodiment 1, the temperature of the contact surface with a subject to be examined should be suppressed within a range of 30~50° C., for example, so as not to cause damage or unpleasantness to the subject to be examined, namely, a living body.

In addition, the prior art provides an ultrasonic probe externally mounted with an acoustic coupler on the probe shell (case). In the case of the ultrasonic probe relating to the prior art, the acoustic coupler for external mounting can be attached and detached, and the probe can be used with the acoustic coupler detached. For this reason, in order to keep the temperature of the top end (contact surface with a subject to be examined) of the ultrasonic probe within the range defined by the above standard when the acoustic coupler for external mounting is detached, the transmission output level of ultrasonic waves should be set. Accordingly, even when the acoustic coupler for external mounting is mounted, the transmission of ultrasonic waves is to be done with the transmission output level set when the acoustic coupler for external mounting is detached.

In the case of ultrasonic probe 1 related to Embodiment 1, as the low attenuation medium 6 is installed inside the probe shell, the transmission output level of ultrasonic waves is set so as to be under the state in which the low attenuation medium 6 is mounted. The transmission output level at this moment can be set higher than the ultrasonic probe relating to the prior art in which the acoustic coupler for external mounting is removed. As described above, the heat generated on the ultrasonic transducer section 3 is difficult to transfer to the top end 1a (contact surface with subject to be examined) of the ultrasonic probe 1 caused by the low attenuation medium installed, thus maintaining the temperature of the contact surface of a subject to be examined to be lower than that of the prior art.

As a result, for the ultrasonic probe 1 related to Embodiment 1, the transmission output level of ultrasonic waves can be set to a higher level than that of the ultrasonic probe mounted with the acoustic coupler for external mounting. This enables ultrasonic waves to be transmitted more deeply inside a subject to be examined (living body) than the ultrasonic probe mounted with the acoustic coupler for external mounting according to the prior art, thus widening the region of observation.

Here, the difference between the ultrasonic probe 1 and the ultrasonic probe according to the prior art with the acoustic coupler for external mounting is summarized. For the ultrasonic probe according to the prior art, the transmission output level is required to be set such that the temperature of the top end (contact surface with a subject to be examined) of the ultrasonic probe is kept within the temperature range defined by the above standard when the acoustic coupler for external mounting is not mounted. For this reason, even under the state when the acoustic coupler for external mounting is mounted, ultrasonic waves are transmitted within the range of the output level set with the acoustic coupler removed.

Contrarily, in the case of the ultrasonic probe 1 according to Embodiment 1, as the low attenuation medium 6 is installed inside the probe shell 7, the transmission output level of ultrasonic waves can be set to a higher level than the ultrasonic probe according to the prior art in which the acoustic coupler for external mounting is removed.

Therefore, when the ultrasonic probe 1 according to Embodiment 1 and the ultrasonic probe according to the prior art in which the acoustic coupler for external mounting is mounted are compared, the transmission level of the ultrasonic probe 1 according to Embodiment 1 can be set to a higher level.

As a result, the higher output level of ultrasonic waves to be transmitted has a higher sensitivity, enabling ultrasonic waves to be transmitted more deeply.

[Embodiment 2]

Figure 6A:
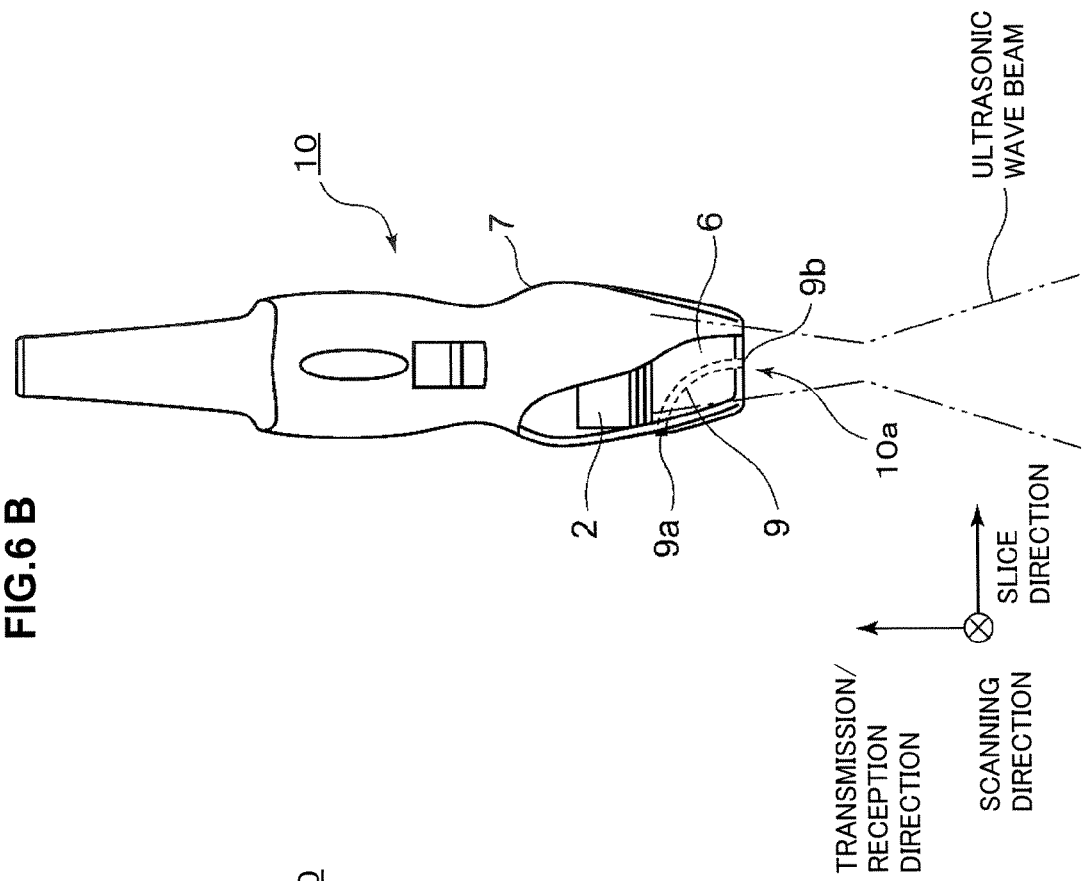
FIG. 6 A represents a front view showing the outline constitution of the head side of the ultrasonic probe according to the second embodiment of the present invention.
Figure 6B:
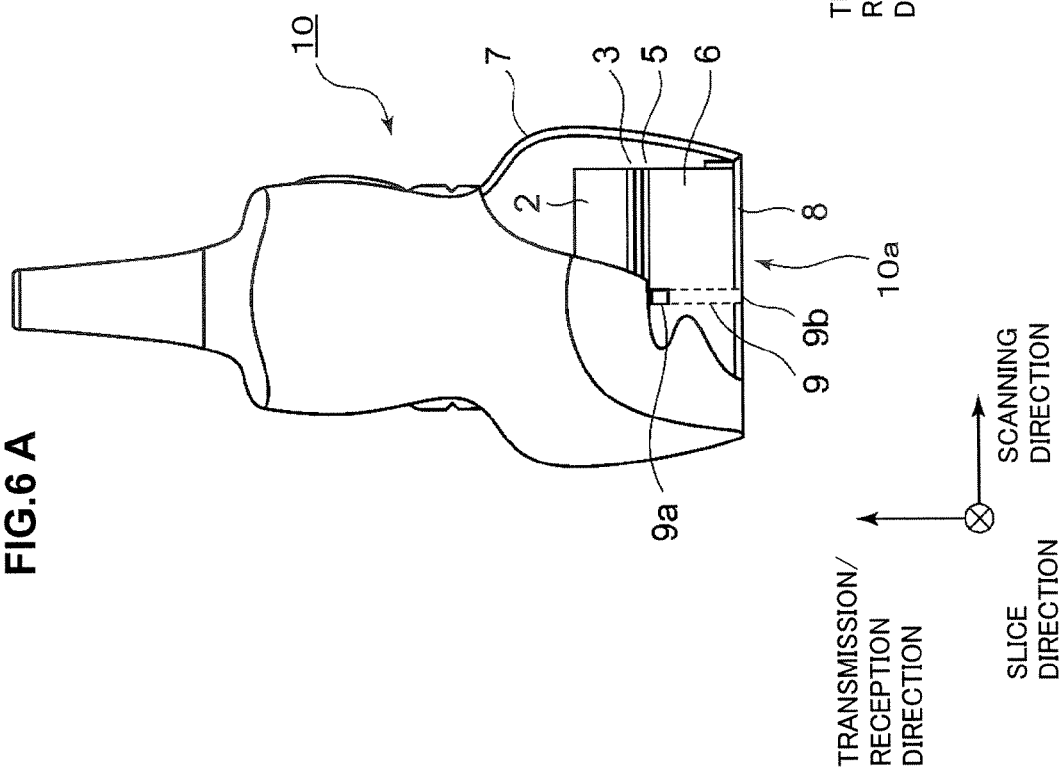
Figure 7:
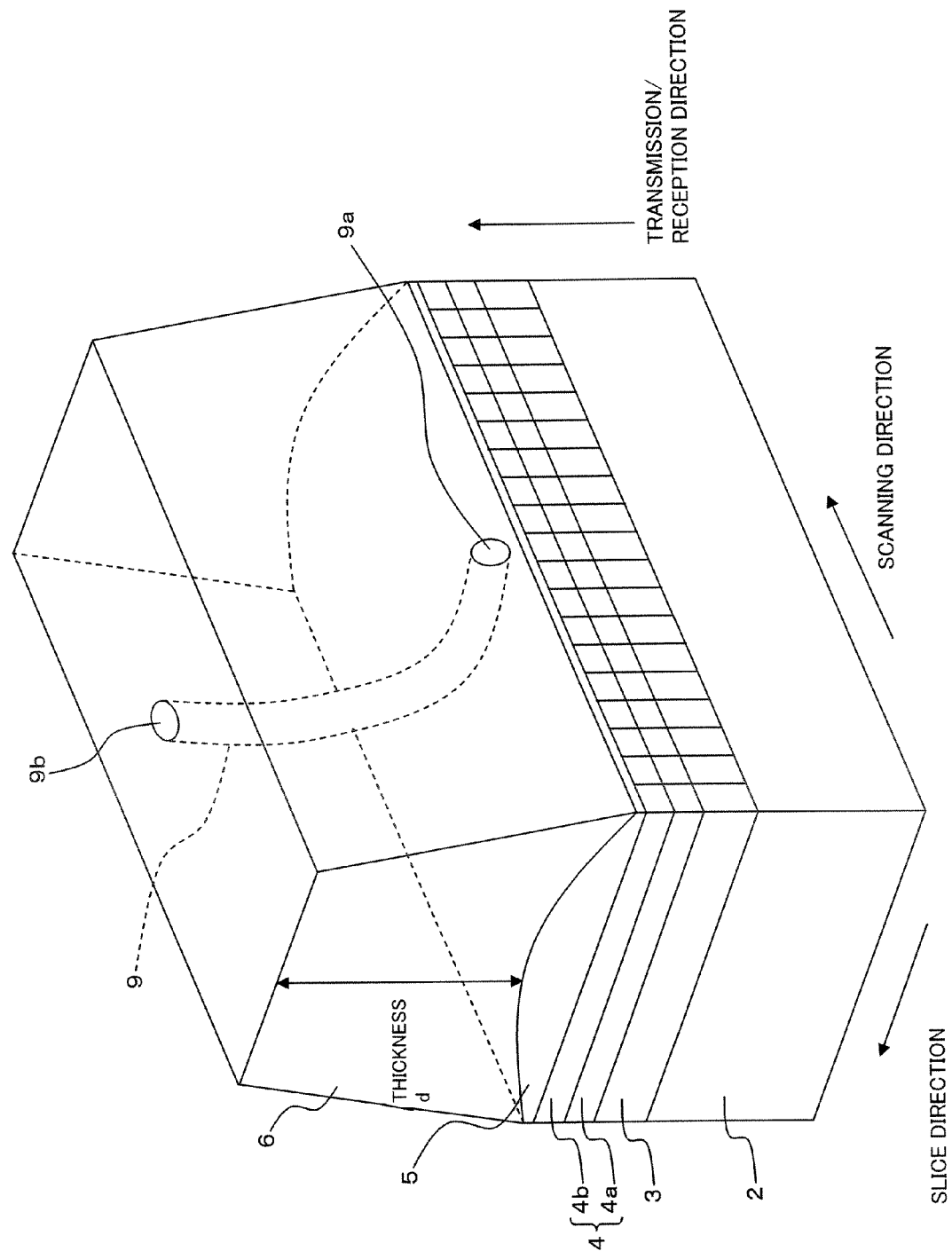
FIG. 7 represents a perspective view showing the outline constitution of the head side of the ultrasonic probe according to the second embodiment of the present invention.

Next, the constitution of the ultrasonic probe relating to Embodiment 2 of the present invention is explained in reference to FIG. 6A, FIG. 6B and FIG. 7. FIG. 6A represents a front view showing the outline constitution of the head side of the ultrasonic probe relating to Embodiment 2 of the present invention. FIG. 6B represents a side view showing the outline constitution of the head side of the ultrasonic probe relating to Embodiment 2 of the present invention. FIG. 6A indicates the ultrasonic probe 10 viewed from the slice direction (direction perpendicular to the scanning direction). FIG. 6B indicates the ultrasonic probe 10 viewed from the scanning direction. In a part of FIG. 6A and FIG. 6B, each of built-in sections is shown.

FIG. 7 represents a perspective view showing the outline constitution of the head side of the ultrasonic probe relating to Embodiment 2 of the present invention. In FIG. 6A, FIG. 6B and FIG. 7, the head side of the ultrasonic probe is shown. In Embodiment 2, similar to Embodiment 1, a so-called one-dimensional ultrasonic probe exists, wherein a plural of ultrasonic transducers are arranged in a row.

As shown in FIG. 7, the ultrasonic probe 10 relating to Embodiment 2 consists of a backing material 2, an ultrasonic transducer section 3, an acoustic matching layer 4 and an acoustic lens 5. Further, a low attenuation medium 6 is installed on the acoustic lens 5 as shown in FIG. 6A, FIG. 6B and FIG. 7 of the ultrasonic probe relating to Embodiment 2.

Further, as shown in FIG. 6A and FIG. 6B, the backing material 2, ultrasonic transducer section 3, acoustic matching layer 4, acoustic lens 5 and low attenuation medium 6 are housed in a probe shell 7 (case). In this case, the low attenuation medium is housed in the probe shell 7 such that it is located at the top end 10a side of the ultrasonic probe 10, namely at the contact surface side to a subject to be examined.

By being constituted as above, the ultrasonic waves transmitted from the ultrasonic transducer section 3 are converged in the slice direction by the acoustic lens 5, and are further radiated to the outside of the ultrasonic probe 10 (transmission/reception direction) through the low attenuation medium 6. The reflection waves from the subject to be examined insolate inside the ultrasonic probe 10 through the low attenuation medium 6, and are received by the ultrasonic transducer section 3 through the acoustic lens 5.

Here, the constitution of the low attenuation medium 6 is explained. As shown in the perspective view of FIG. 7, the surface (contacting the low attenuation medium 6) of the acoustic lens 5 is convex. The surface of the low attenuation medium 6 contacting the acoustic lens 5 (the first surface) is formed in a concave configuration to couple with the curved convex surface of the acoustic lens 5. Also, the low attenuation medium 6 is formed tapering towards the top, with the width of the low attenuation medium 6 in the direction of the slice direction narrowing gradually in the direction away from the acoustic lens 5 (transmission/reception direction). In other words, the sectional area perpendicular to the transmission/reception direction of the low attenuation medium 6 is formed such that it gradually shrinks in the direction away from the acoustic lens 5, and the area of the surface opposing the first surface (surface of the top end 1a side of the ultrasonic probe (the second surface)) is formed to be smallest.

Further, a puncture needle guide 9 is installed on the low attenuation medium 6 to guide a puncture needle into a subject to be examined (living body). The puncture needle guide 9 is cylindrical with both ends opened in order to guide the puncture needle into the subject to be examined (living body) for penetration. This puncture needle guide 9 is bent at a specified curvature and installed covering from the side surface along the scanning direction of the low attenuation medium 6 to the surface of the top end 10a side (the second surface).

The inlet 9a (other end) of the puncture needle guide 9 is on the side surface of the low attenuation medium 6, and is formed on the surface along the scanning direction (arrangement direction of ultrasonic transducers). Further, the direction of the inlet 9a is perpendicular to the plane including the transmission/reception direction of ultrasonic waves (transmission/reception direction) and the ultrasonic transducer arrangement direction (surface on which tomography image is formed). For the probe shell 7, an opening is formed (not shown in the figure) at the position corresponding to that of the inlet 9a of the puncture needle guide 9, through which puncture needles can enter/exit. In this Embodiment 2, the opening (not shown in the figure) is formed on the side surface of the probe shell 7 along the scanning direction.

The outlet 9b (one end) of the puncture needle guide 9 is formed on the surface of the top end 10a side of the low attenuation medium 6 (the second surface). The puncture needle guided through the inlet 9a is guided to the outside of the ultrasonic probe 10 from the outlet 9b through the puncture needle guide 9. The outlet 9b of the puncture needle guide 9 is directed perpendicular to the plane (on which the tomography image is formed) in the direction of the transmission/reception of ultrasonic waves (transmission/reception direction) and the direction in which the ultrasonic transducers are arranged (scanning direction). As explained, since the direction of the outlet 9b is perpendicular to the plane (on which the tomography image is formed) in the transmission/reception direction and scanning direction, a puncture needle can be injected into a living body along the plane which forms the tomography image.

In Embodiment 2, the direction of the outlet 9b of the puncture needle guide 9 is perpendicular to the top end 10a of the ultrasonic probe 10. In other words, the direction of the outlet 9b is perpendicular to the scanning direction and slice direction. Due to this, a puncture needle can be guided externally in a substantially vertical state from the outlet 9b of the puncture needle guide 9, and as a result, the puncture needle can be injected into a subject to be examined (living body) in a substantially vertical state.

In Embodiment 2, the direction of the outlet 9b of the puncture needle guide 9 is arranged so as to be perpendicular to the top end 10a; however, it may be formed slanting to the top end 10a if it is parallel with the plane (on which the tomography image is formed) in the transmission/reception direction and scanning direction. Even in this case, a puncture needle can be injected into a living body along the plane on which the tomography image is formed.

Here, the outlet 9b of the puncture needle guide 9 is preferably formed near the center of the slice direction at the top end 10a of the ultrasonic probe 10. This allows the puncture needle to be introduced at substantially the center of the beam of ultrasonic waves narrowed down by the acoustic lens 5.

The outlet 9b of the puncture needle guide 9 is preferably formed near the center of the scanning direction at the top end 10a of the ultrasonic probe 10. This allows the puncture needle to be introduced at substantially the center of the tomography image and depict the puncture needle at the substantially center of the tomography image.

The puncture needle guide 9 is formed by metal or resin.

By changing the diameter of the puncture needle guide 9, a plural of types of puncture needles with different diameters can be used.

The thickness d of the low attenuation medium 6 in the direction of transmission/reception, similar to Embodiment 1, is preferably determined based on the characteristic of the sound field distribution of the ultrasonic transducer section 3. Similar to Embodiment 1, the thickness d of the low attenuation medium 6 is preferably set to exceed the required distance to stabilize the sound field of ultrasonic waves.

By adjusting the thickness d of the low attenuation medium 6 similar to Embodiment 1, the focus position in the slice direction of ultrasonic waves can be formed outside of the ultrasonic probe 10. This allows the focus position in the slice direction of ultrasonic waves to be formed inside a subject to be examined (living body) enabling a clear image inside the subject to be examined (living body) to be obtained.

A thin protective film 8 may be installed on the top end 10a (contacting a living body) of the ultrasonic probe 10 similar to Embodiment 1. This protective film 8 is installed to secure the safety of the subject to be examined and the durability of the low attenuation medium 6.

(Action)

According to the ultrasonic probe 10 with the above constitution, the same action and effect as that of the ultrasonic probe 1 according to Embodiment 1 can be obtained. Namely, (1) a clear image can be obtained near the surface of a living body. (2) The area of the top end 10a (contacting a subject to be examined) of the ultrasonic probe 10 can be reduced, improving the operability of the ultrasonic probe 10 as a result. (3) The sensitivity of the ultrasonic probe 10 can be increased. (4) Ultrasonic waves containing a higher harmonic component can be received even near the surface of a living body, and as a result, a highly precise image with high resolution can be obtained near the surface of a living body. (5) When making the transmission output level of ultrasonic waves equal to the ultrasonic probe according to the prior art, the temperature of the top end 10a of the ultrasonic probe 10 can be lowered compared to the prior art. As a result, the transmission output level of ultrasonic waves can be raised while keeping the temperature of the contact surface with a subject to be examined lower than or equal to the temperature of the contact surface of the ultrasonic probe according to the prior art. Due to this, ultrasonic waves can be transmitted to a deeper position inside a subject to be examined (living body).

Further according to the ultrasonic probe 10 relating to Embodiment 2, (6) a puncture needle can be identified by an ultrasonic wave image at a stage before injecting the puncture needle into the body surface, providing a safe puncture method.

By installing the low attenuation medium 6 onto the acoustic lens 5, the tomography image of the low attenuation medium 6 can be depicted. Also, by installing the puncture needle guide 9 onto the low attenuation medium 6, the puncture needle at a stage before injecting into the subject to be examined (living body) guided through the low attenuation medium 6 can be depicted in the tomography image, thus allowing the puncture needle to be identified on the tomography image at a stage before injecting it into the living body. Further, as the outlet 9b of the puncture needle guide 9 is arranged in parallel with the plane (on which the tomography image is formed) in the transmission/reception direction and scanning direction, the puncture needle can be injected into a living body along the plane forming the tomography image. As explained, as the position of the puncture needle can be identified by the tomography image at a stage before being injected into the living body, a safe puncture method can be provided.

According to the ultrasonic probe 10 relating to Embodiment 2, it is not necessary to form a notch on a part of the ultrasonic transducer section, although this is required by the prior art, and an ultrasonic wave image without uneven luminance due to the notch can be obtained.

Moreover, as the ultrasonic probe 10 relating to Embodiment 2 has a constant width in the direction of the low attenuation medium 6, it is suitable for use with linear scanning, and is applicable for convex scanning also without driving the ultrasonic transducer installed on the end section of the ultrasonic transducer section 3.

[Embodiment 3]

Figure 9:
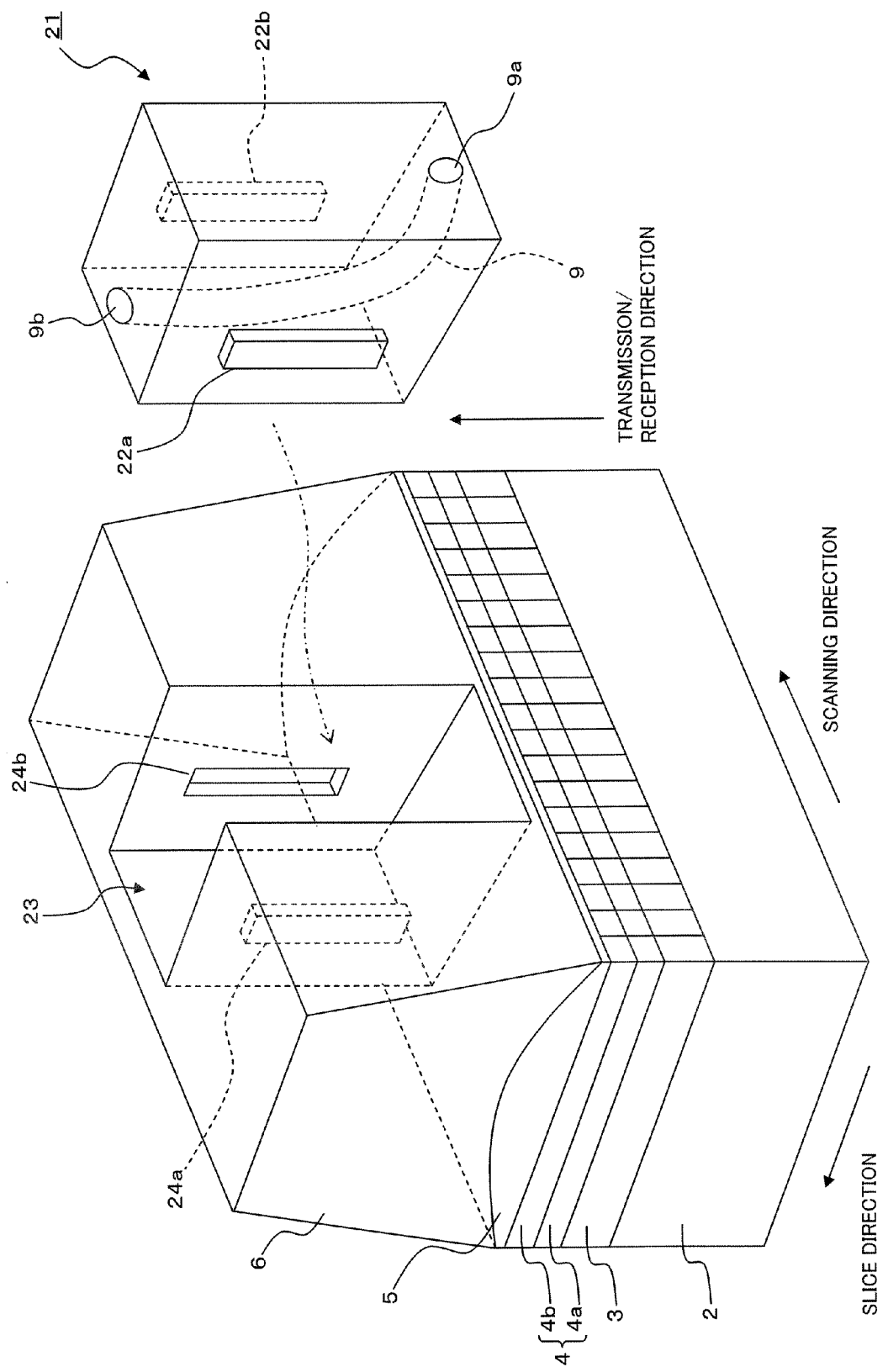
FIG. 9 represents a perspective view showing the outline constitution of the head side of the ultrasonic probe according to the third embodiment of the present invention.

Next, the constitution of the ultrasonic probe relating to Embodiment 3 of the present invention is explained in reference to FIG. 8 and FIG. 9. FIG. 8 represents a front view showing the outline constitution of the head side of the ultrasonic probe relating to Embodiment 3 of the present invention. In a part of FIG. 8, each of built-in sections is shown. FIG. 9 represents a perspective view showing the outline constitution of the head side of the ultrasonic probe relating to Embodiment 3 of the present invention. In Embodiment 3, similar to Embodiment 1, an explanation is provided for the so-called one-dimensional ultrasonic probe, wherein a plural of ultrasonic transducers are arranged in a row in the scanning direction. For the ultrasonic probe 10 relating to Embodiment 2 explained above, the puncture needle guide 9 is directly formed on the low attenuation medium 6, while for the ultrasonic probe 20 relating to Embodiment 3, the puncture needle guide 9 is arranged so as to be detachable from the low attenuation medium 6.

As shown in FIG. 9, a notch 23 cut off in a specified shape is formed on the low attenuation medium 6. For the notch 23, a coupling member 21 to match the shape of the notch is inserted and secured to the low attenuation medium 6.

On the coupling member 21, similar to the ultrasonic probe 10 relating to said Embodiment 2, a puncture needle guide 9 bent at a specified curvature is installed. By the insertion of coupling member 21 into the notch 23, the puncture needle guide 9 is installed to cover from the side of the low attenuation medium 6 to the surface of the top end 20a (the second surface). The shape of the puncture needle guide 9 and the direction of the inlet 9a and outlet 9b are the same as the puncture needle guide 9 installed on the ultrasonic probe 10 relating to said Embodiment 2. On the probe shell 7, similar to said Embodiment 2, an opening (not shown in the figure) is formed at a position corresponding to the inlet 9a of the puncture needle guide 9, allowing the puncture needle to enter/exit through the opening. In Embodiment 3, an opening (not shown in the figure) is formed on the side of the probe shell 7 along the scanning direction.

On the one side of the coupling member 21, a convex 22a is formed, while on the opposite surface, another convex 22b is formed. Further, on the notch 23 formed on the low attenuation medium 6, a concave 24a to be coupled with the convex 22a of the coupling member 21 is formed, and on the surface opposite to the concave 24a, a convex 24b to be coupled with the convex 22b of the coupling member 21 is formed. Further, insertion of the coupling member 21 into the notch 23 of the low attenuation medium 6 couples the convex 22a of the coupling member 21 and the concave 24a of the notch 23, and couples the convex 22b of the coupling member 21 and the concave 24b of the notch 23. This mounts the coupling member 21 on the low attenuation medium 6.

The same material of the low attenuation medium 6 is used for the coupling member 21.

When imaging without using a puncture needle, a dummy member of the same external shape as the coupling member 21 and without the puncture needle guide 9 formed is inserted into the notch 23 to conduct imaging without using a puncture needle.

By preparing a plural of coupling members 21, and installing the puncture needle guide 9 with a different diameter according to each coupling member 21, a puncture needle guide 9 with a different diameter can be installed on the ultrasonic probe simply by replacing the coupling member 21. In this way, a puncture needle with a different diameter can be applied.

(Action)

According to the ultrasonic probe 20 having the above constitution, the same action and effect of the ultrasonic probe 10 related to Embodiment 2 described above can be obtained. Namely, according to the ultrasonic probe 20, the same action and effect of the ultrasonic probe 1 relating to Embodiment 1 can be obtained, and a puncture needle can be identified by an ultrasonic wave image at a stage before injecting the puncture needle into a living body surface, thus providing a safe puncture needle method.

For the ultrasonic probe 20 related to Embodiment 3, the convex 22a and 22b are installed on the coupling member 21, and the concave 24a and concave 24b are installed on the notch 23; however, the convex or concave may not be installed. For example, by inserting the coupling member 21 into the notch 23, the coupling member 21 may be secured to the notch 23 by utilizing the friction between the coupling member 21 and the low attenuation medium 6.

[Embodiment 4]

Figure 10:
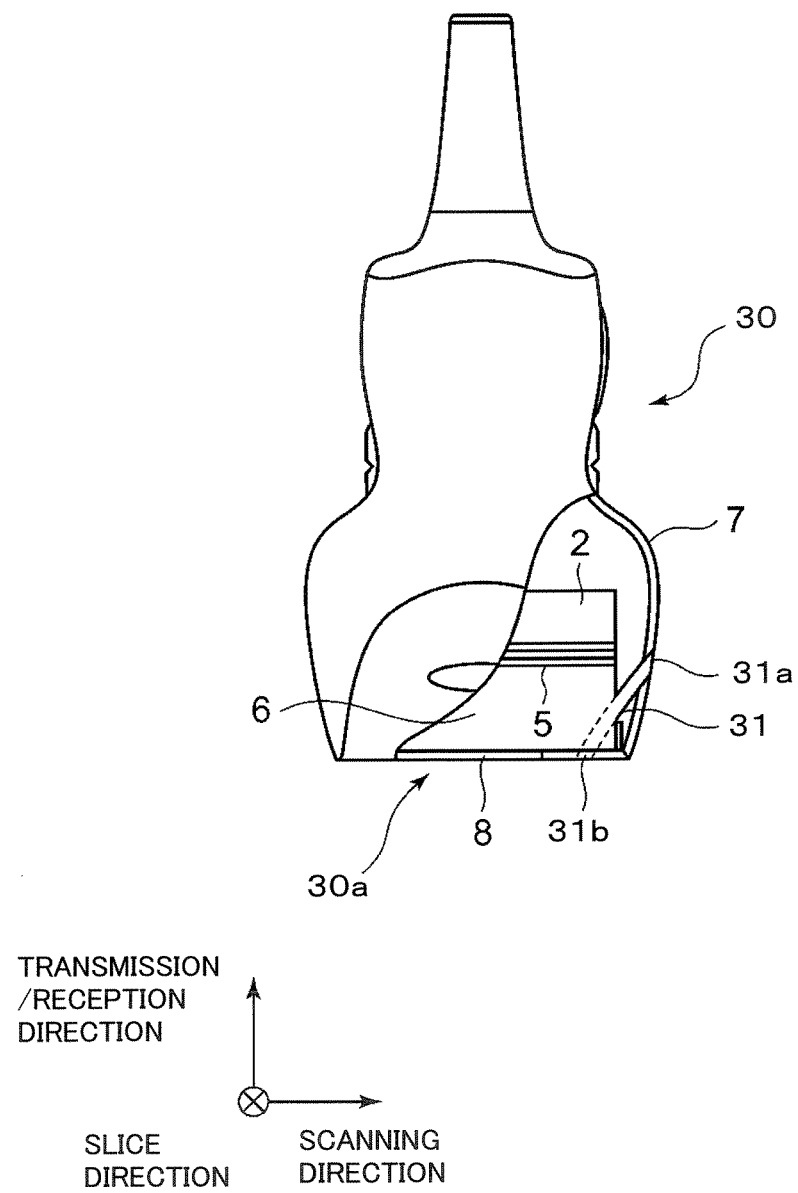
FIG. 10 represents a front view showing the outline constitution of the head side of the ultrasonic probe according to the fourth embodiment of the present invention.
Figure 11:
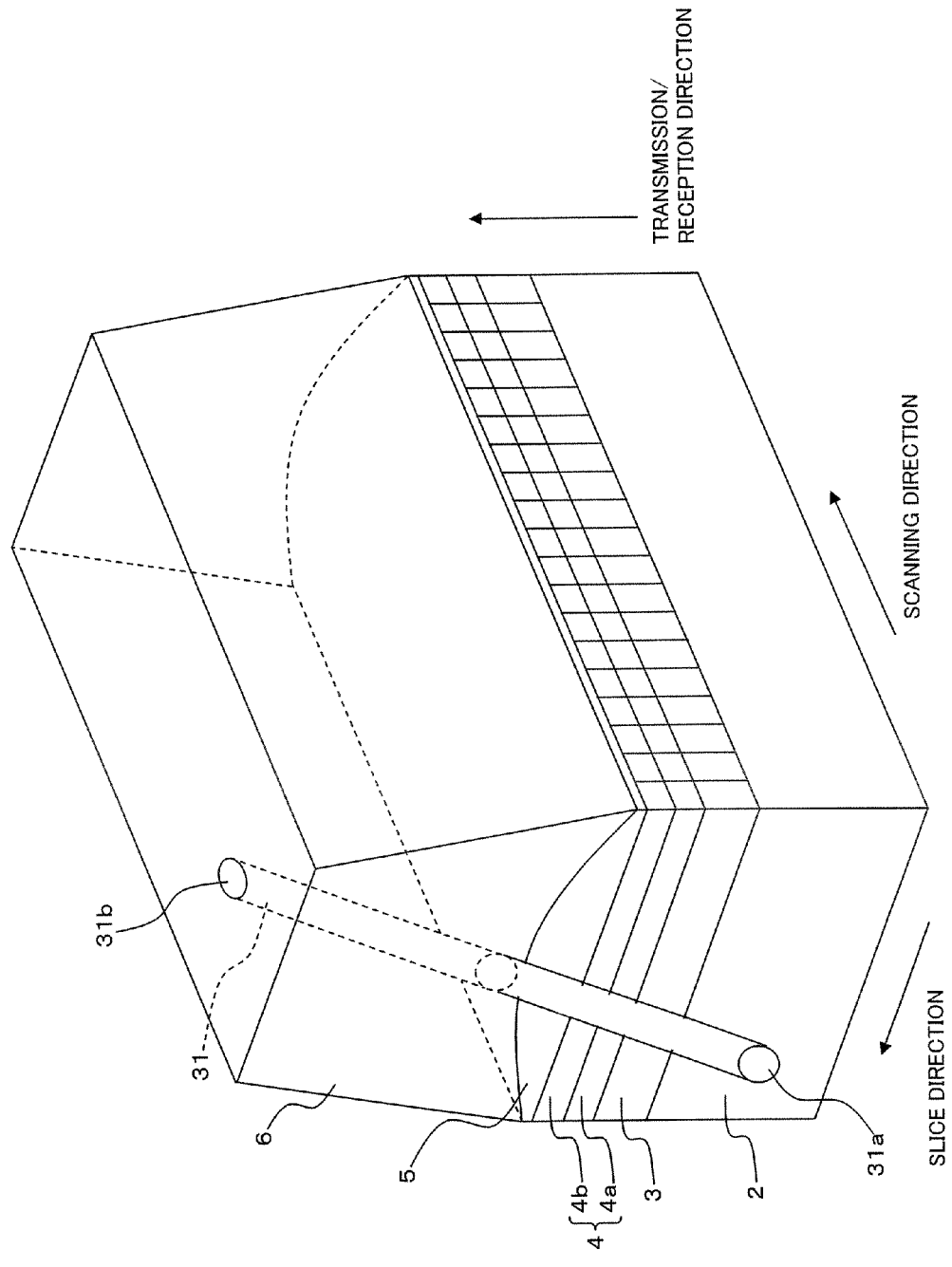
FIG. 11 represents a perspective view showing the outline constitution of the head side of the ultrasonic probe according to the fourth embodiment of the present invention.
Figure 12:
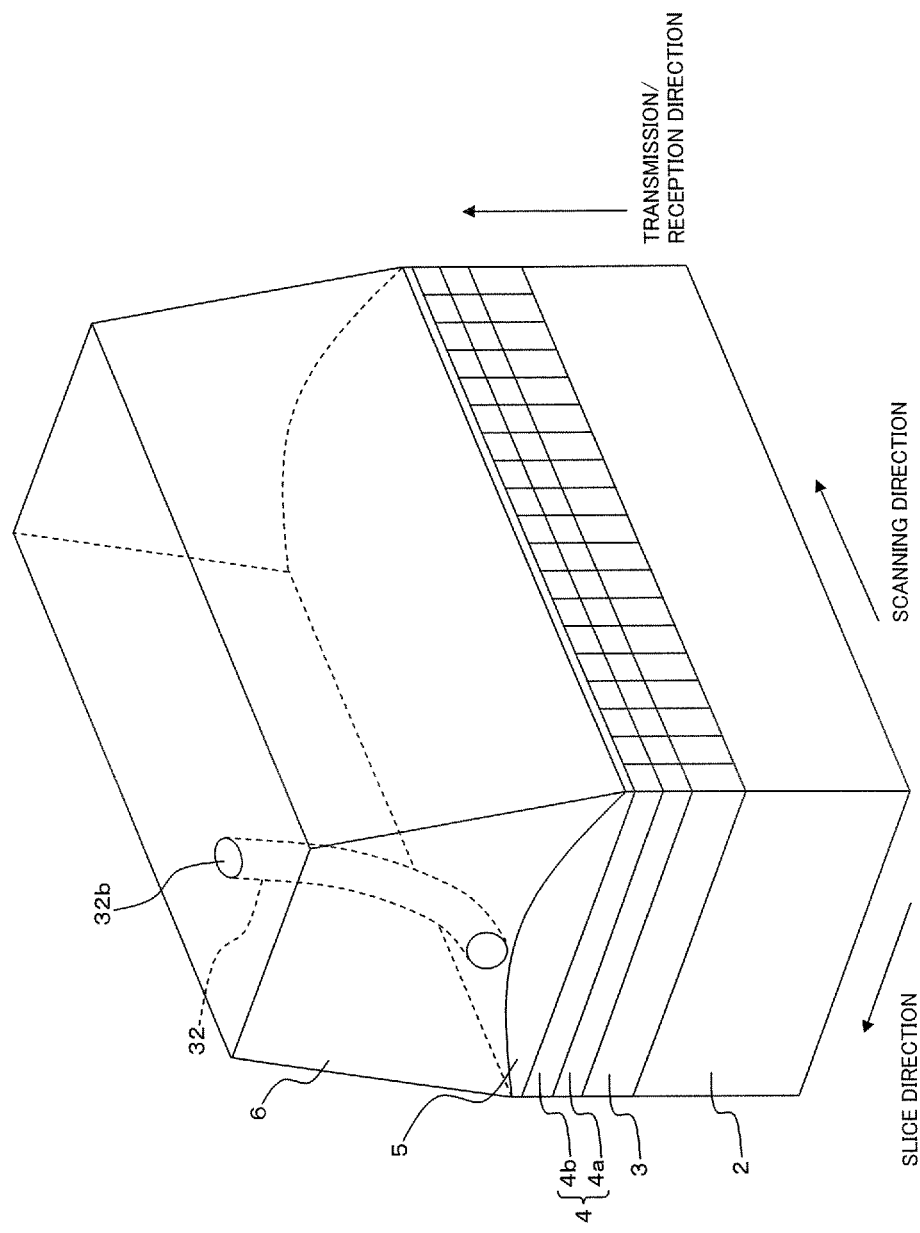
FIG. 12 represents a perspective view showing the outline constitution of the head side of the ultrasonic probe according to the fourth embodiment of the present invention.

Next, the constitution of the ultrasonic probe related to Embodiment 4 of the present invention is explained in reference to FIG. 10 to FIG. 12. FIG. 10 represents a front view showing the head side of the ultrasonic probe related to Embodiment 4 of the present invention. In FIG. 10, a part of the drawings indicates each section being housed. FIG. 11 and FIG. 12 represent a perspective view showing the outline of the head side of the ultrasonic probe related to Embodiment 4 of the present invention. In Embodiment 4, similar to Embodiment 1, an explanation is provided for a so-called one-dimensional ultrasonic probe, wherein a plural of ultrasonic transducers are arranged in a row in the direction of the scanning.

As shown in FIG. 10 and FIG. 11, at the ultrasonic probe 30 related to Embodiment 4, a linear state puncture needle guide 31 is installed on the low attenuation medium 6, instead of the puncture needle guide 9 installed on the ultrasonic probe related to Embodiment 2 stated above. The puncture needle guide 31 is formed by metal or resin similar to the puncture needle guide 9, and is formed as a cylinder with both ends open so as to guide the puncture needle to the subject to be examined (living body) through the opening. In Embodiment 4, the puncture needle guide 31 is installed in parallel to the plane (on which the tomography image is formed) in the transmission/reception direction and the scanning direction.

As shown in FIG. 11, the puncture needle guide 31 is installed passing through the side along the slice direction of the low attenuation medium 6 (direction perpendicular to the scanning direction) and covering from the side along the slice direction to the surface (the second surface) of the top end 30a side. By installing in this way, the puncture needle introduced from the inlet 31a installed on the side along the slice direction, passes through the puncture needle guide 31 and is guided to the outside of the ultrasonic probe 30 from the outlet 30b installed at the top end 30a side. The outlet 31b of the puncture needle guide 31 is directed in parallel with the plane (on which tomography image is formed) in the transmission/reception and the scanning direction. As explained, as the direction of the outlet 31b is in parallel with the plane forming the tomography image on it, injection of the puncture needle into a living body along the plane forming the tomography image can be performed.

For the probe shell 7, an opening (not shown in the figure) is formed at a position corresponding to the position of the inlet 31a of the puncture needle guide 31 similar to Embodiment 2 described above, making it possible for the puncture needle to enter or exit through the opening. In Embodiment 4, an opening (not shown in the figure) is formed on the side surface of the probe shell 7 installed along the slice direction.

As shown in FIG. 12, the puncture needle guide 32 may be bent at a specified curvature. This puncture needle guide 32 is also installed in parallel with the plane (on which tomography image is formed) in the transmission/reception direction and scanning direction. Near the outlet 32b, the puncture needle guide 32 is formed perpendicular to the top end 30a. This allows the puncture needle to be introduced externally in a state substantially vertical from the outlet 32b of the puncture needle guide 32, enabling the puncture needle to be injected into the body surface of a subject to be examined (living body) in a substantially vertical state.

(Action)

According to the ultrasonic probe 30 having the above constitution, the same action and effect of the ultrasonic probe 10 related to Embodiment 2 described above can be obtained. Namely, according to the ultrasonic probe 30, the same action and effect of the ultrasonic probe 1 related to Embodiment 1 can be obtained, and a puncture needle can be identified by an ultrasonic wave image at a stage before injecting the puncture needle into a living body surface, thus providing a safe puncture needle method.

[Embodiment 5]

Figure 13:
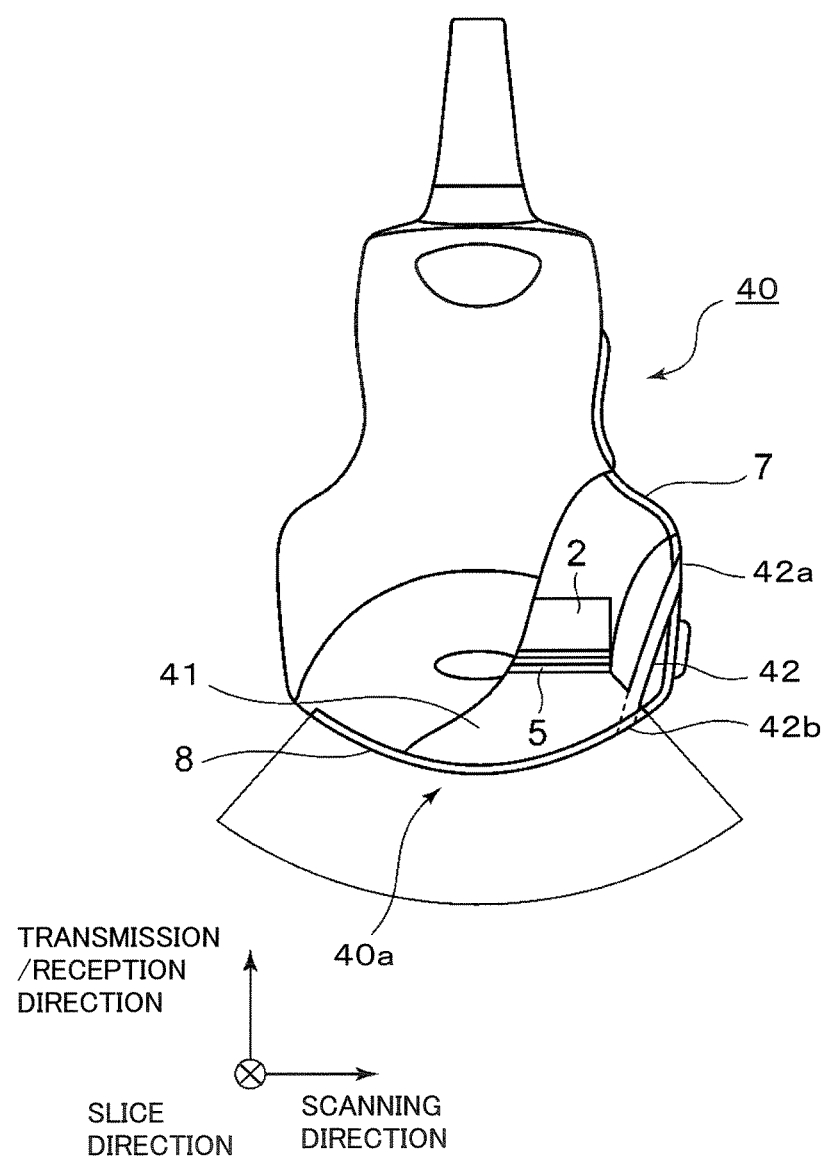
FIG. 13 represents a front view showing the outline constitution of the head side of the ultrasonic probe according to the fifth embodiment of the present invention.

Next, the constitution of the ultrasonic probe related to Embodiment 5 of the present invention is explained in reference to FIG. 13. FIG. 13 represents a front view showing the outline constitution of the head side of the ultrasonic probe related to Embodiment 5 of the present invention. In FIG. 13A, a part of the drawings indicates each housed section. In Embodiment 5, similar to Embodiment 1, an explanation is provided for a so-called one-dimensional ultrasonic probe, wherein a plural of ultrasonic transducers are arranged in a row in the direction of the scamming.

In the ultrasonic probe 40 related to Embodiment 5, similar to the ultrasonic probe 10 related to Embodiment 2 described above, the probe shell 7 houses a rear surface material 2, ultrasonic transducer section 3, acoustic matching layer 4, and acoustic lens 5. The ultrasonic probe 40 houses a low attenuation medium 41 inside the probe shell 7 instead of the low attenuation medium 6 related to Embodiment 2. The low attenuation medium 41 uses the same material as the low attenuation medium 6 related to Embodiment 1.

In the low attenuation medium 41, the surface contacting the acoustic lens 5 is formed flat, while the surface opposing the surface contacting the acoustic lens 5 (surface of the top end 40a of the ultrasonic probe 40) is formed convex. The width of the scanning direction of the low attenuation medium 41 widens gradually from the surface contacting the acoustic lens 5 to the top end 40a side. By the above, as the low attenuation medium 41 is formed in a convex shape, convex scanning can be performed by forming the scanning shape of ultrasonic waves as a base shape.

In the low attenuation medium 41, a linear shape puncture needle guide 42 is installed. The puncture needle guide 42 is formed by metal or resin similar to the puncture needle guide 9 of Embodiment 2, and is formed as a cylinder with both ends open working as a penetrating hole to introduce the puncture needle into a subject to be examined (living body). The puncture needle guide 42 is installed in parallel to the plane (on which the tomography image is formed) in the transmission/reception direction and scanning direction.

The puncture needle guide 42 is installed passing through the side along the slice direction of the low attenuation medium 41, and covering from the side along the slice direction to the surface (the second surface) of the top end 40a side. By being installed in this way, the puncture needle introduced from the inlet 42a installed at the side surface along the slice direction is guided outside the ultrasonic probe 40 from the outlet 42b installed at the top end 40a side through the puncture needle guide 42. The outlet 42b of the puncture needle guide 42 is directed in parallel with the plane including the transmission/reception direction and scanning direction. As explained, as the direction of the outlet 42b is parallel to the plane forming the tomography image, a puncture needle can be injected into a living body along the plane forming the tomography image.

For the probe shell 7, an opening (not shown in the figure) is formed at a position corresponding to the position of the inlet 42a of the puncture needle guide 42 similar to Embodiment 2 described above, making it possible for the puncture needle to enter or exit through the opening. In Embodiment 5, an opening (not shown in the figure) is formed on the side surface of the probe shell 7 being installed along the slice direction.

The puncture needle guide 42 may be bent at a specified curvature. In this case, the puncture needle guide 42 is formed perpendicular to the top end 40a near the outlet 42b. This allows the puncture needle to be introduced out of the outlet 42b of the puncture needle guide 42 enabling the puncture needle to be injected into the body surface of a subject to be examined (living body) in a substantially vertical state as a result.

(Action)

According to the ultrasonic probe 40 having the above constitution, the same action and effect of the ultrasonic probe 10 related to Embodiment 2 described above can be obtained. Namely, according to the ultrasonic probe 40, the same action and effect of the ultrasonic probe 1 related to Embodiment 1 can be obtained, and a puncture needle can be identified by an ultrasonic wave image at a stage before injecting the puncture needle into a living body surface, thus providing a safe puncture needle method.

In addition, it is not necessary that the puncture needle guide 42 be installed on the low attenuation medium 41. In this case, the image obtained by the ultrasonic probe 40 depicts the living body side of the contact surface of the subject to be examined.

[Embodiment 6]

Figure 14:
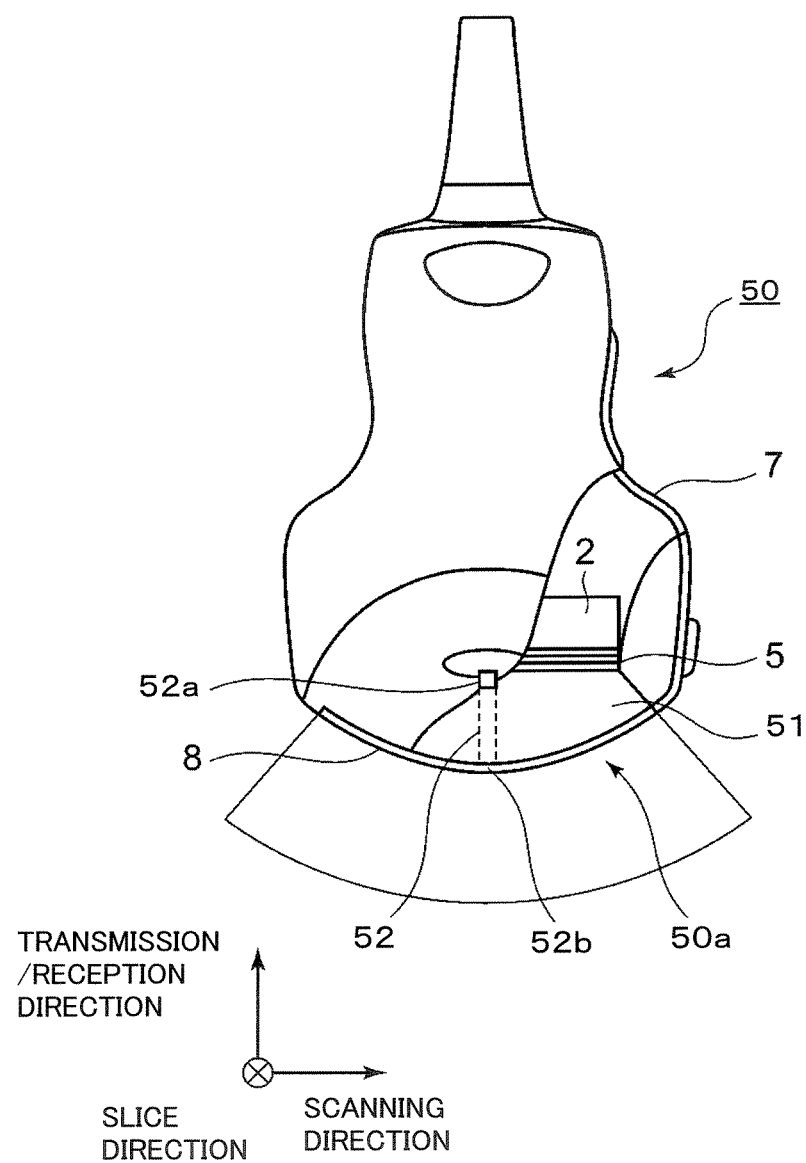
FIG. 14 represents a front view showing the outline constitution of the head side of the ultrasonic probe according to the sixth embodiment of the present invention.

Next, the constitution of the ultrasonic probe related to Embodiment 6 of the present invention is explained in reference to FIG. 14. FIG. 14 represents a front view showing the head side of the ultrasonic probe related to Embodiment 6 of the present invention. In FIG. 14, a part of the drawings indicates each housed section. In Embodiment 6, similar to Embodiment 1, an explanation is provided for a so-called one-dimensional ultrasonic probe, wherein a plural of ultrasonic transducers are arranged in a row in the direction of the scanning.

In the ultrasonic probe 50 related to Embodiment 6, similar to the ultrasonic probe 40 according to the above-mentioned Embodiment 5, houses a low attenuation medium 51 formed in a convex shape. The low attenuation medium 51 is installed with the puncture needle guide 52 bent at a specified curvature, similar to the low attenuation medium 6 according to Embodiment 2. Also, the inlet 52a (other end) of the puncture needle guide 52 is formed in a plane along the scanning direction of the low attenuation medium 51. The outlet 52b (one end) of the penetrating hole 52 is formed in the surface (second surface) of the top end 50a side of the low attenuation medium 51, and in parallel to the plane (on which the tomography image is formed) in the transmission/reception direction and scanning direction. As the direction of the outlet 52b is in parallel to the plane forming the tomography image, the puncture needle introduced from the inlet 52a is guided to the outside of the ultrasonic probe 50 from the outlet 52b through the puncture needle guide 52. In doing so, the puncture is injected into a living body along the plane forming the tomography image.

For the probe shell 7, an opening (not shown in the figure) is formed at a position corresponding to the position of the inlet 52a of the puncture needle guide 52 making it possible for the puncture needle to enter or exit through the opening. In Embodiment 6, an opening (not shown in the figure) is formed on the side surface of the probe shell 7 installed along the slice direction.

Moreover, the low attenuation medium 51 uses the same material as that of the low attenuation medium 6 in Embodiment 1. Also, the puncture needle guide 52 is formed from metal or resin similarly to Embodiment 2.

(Action)

According to the ultrasonic probe 50 having the above constitution, the same action and effect of the ultrasonic probe 10 related to Embodiment 2 described above can be obtained. Namely, according to the ultrasonic probe 50, the same action and effect of the ultrasonic probe 1 related to Embodiment 1 can be obtained, and a puncture needle can be identified by an ultrasonic wave image at a stage before injecting the puncture needle into a living body surface, thus providing a safe puncture needle method.

In addition, similar to the ultrasonic probe 40 related to Embodiment 5 described above, as the low attenuation medium 51 is formed in convex, convex scanning can be performed by forming the scanning by ultrasonic waves as a base shape.

[Embodiment 7]

Figure 15:
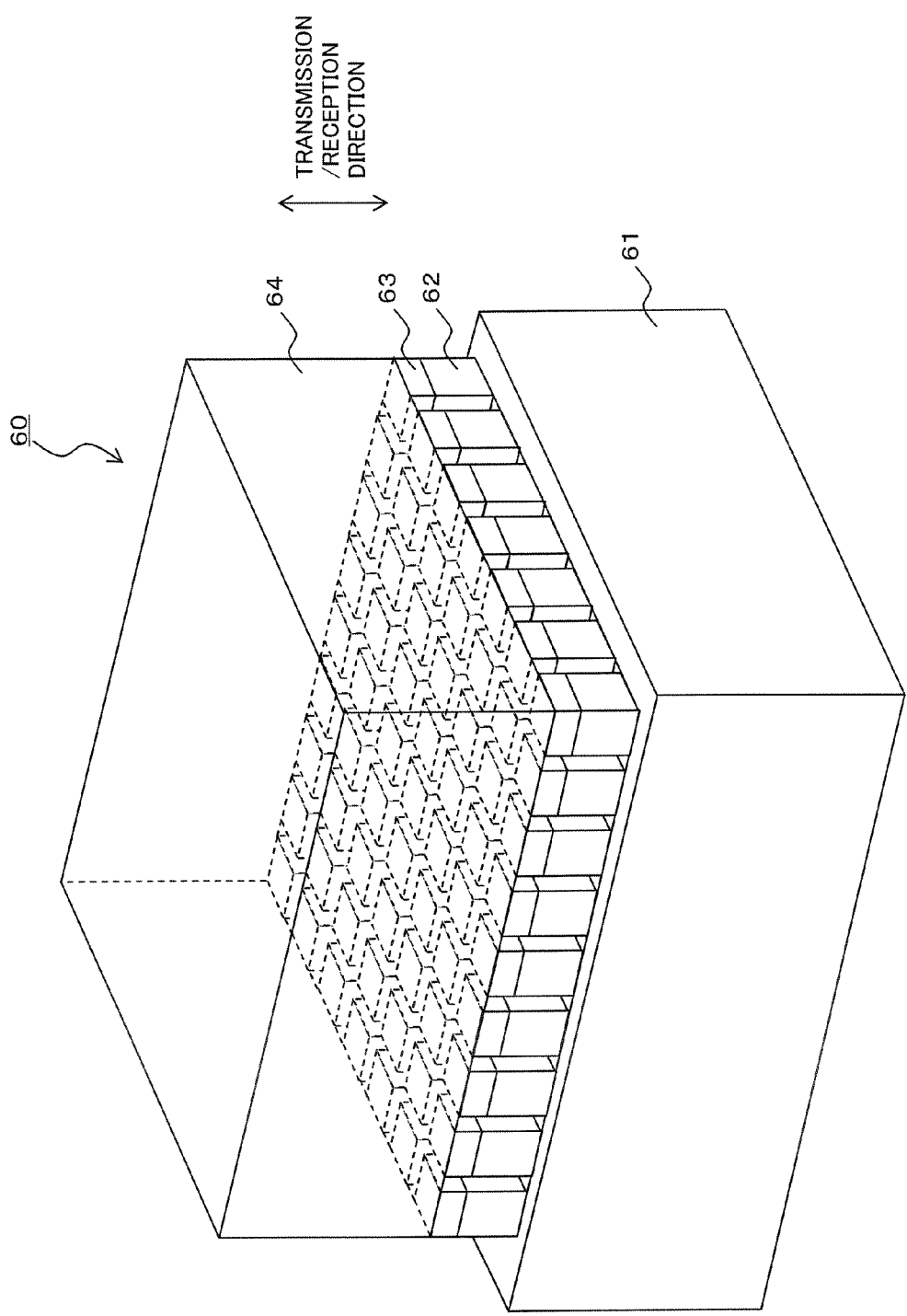
FIG. 15 represents a perspective view showing the outline constitution of the head side of the ultrasonic probe according to the seventh embodiment of the present invention.

Next, the constitution of the ultrasonic probe related to Embodiment 7 of the present invention is explained in reference to FIG. 15. FIG. 15 represents a perspective view showing the outline constitution of the head side of the ultrasonic probe related to Embodiment 7 of the present invention. FIG. 15 shows the head side of the ultrasonic probe. From Embodiment 1 to Embodiment 6, a so-called one-dimensional ultrasonic probe in which a plural of ultrasonic transducers arranged in a row in the direction of the scanning was explained. In this Embodiment 7, an explanation is provided for a so-called two-dimensional ultrasonic wave, wherein a plural of ultrasonic transducers are arranged in a two-dimensional configuration.

The ultrasonic probe 60 related to Embodiment 7 comprises an ultrasonic transducer section 62 having a plural of ultrasonic transducers arranged in a lattice pattern. A channel (gap) is provided between individual ultrasonic transducers, and the plural of ultrasonic transducers are arranged two-dimensionally taking up space over the channel. Although not shown in the figure, an electrode is installed on both surfaces of the ultrasonic transducer section 62. The signal may also pass through the lower surface of the ultrasonic transducer section 62 and the upper surface of the acoustic matching layer 63.

On the one surface of the ultrasonic transducer section 62, an acoustic matching layer 63, and on the opposite surface, a backing material 61 are installed. Similar to the ultrasonic transducer section 62, the acoustic matching layer 63 is divided by a channel. Although an acoustic matching layer 63 is installed in one layer, the acoustic matching layer may be installed in two or more layers. Further, for the ultrasonic probe 60 according to Embodiment 7, a low attenuation medium 64 is installed on the acoustic matching layer 63. The low attenuation medium 64 uses the same material as the low attenuation medium 6 according to Embodiment 1.

Moreover, a backing material 61, an ultrasonic transducer section 62, an acoustic matching layer 63, and a low attenuation medium 64 are housed in the probe shell (not shown in the figure). At this time, the low attenuation medium 64 is housed in the probe shell to be placed at the top end (contact surface with a subject to be examined) of the ultrasonic probe.

Due to the above constitution, the ultrasonic waves transmitted from the ultrasonic transducer section 62 are radiated to the outside of the ultrasonic probe 60 through the low attenuation medium 64. The reflection waves from a subject to be examined insolate into the ultrasonic probe 60 through the low attenuation medium 64, after which they are received by the ultrasonic transducer section 62.

The low attenuation medium 64 has a cubic or rectangular parallel-piped shape. The thickness of the low attenuation medium 64 in the transmission/reception direction is preferably determined based on the characteristic of the sound field distribution of the ultrasonic transducer section 62 similar to Embodiment 1. It is preferable to make the thickness d of the low attenuation medium 64 greater than that providing a stable sound field of ultrasonic waves.

By adjusting the thickness d of the low attenuation medium 64 similar to Embodiment 1, the focus position in the slice direction of ultrasonic waves can be formed outside of the ultrasonic probe 60. In doing so, the focus position in the slice direction of ultrasonic waves can be formed inside a subject to be examined (living body), thus allowing a clear image inside the subject to be examined (living body) to be obtained.

(Action)

According to the ultrasonic probe 60 having the above constitution, the same action and effect of the ultrasonic probe 1 related to Embodiment 1 can be obtained. Namely, (1) a clear image can be obtained near a living body surface. (2) The sensitivity of the ultrasonic probe 60 can be increased. (3) Ultrasonic waves containing a higher harmonic component can be received even from a living body surface, enabling a highly precise image with high resolution to be obtained near the living body surface resultantly. (4) When making the transmission output level of ultrasonic waves equal to the ultrasonic probe relating to the prior art, the temperature at the top end (contact surface with a subject to be examined) of the ultrasonic probe 60 can be lowered compared to the prior art. In this way, the transmission output level of ultrasonic waves can be raised while keeping the contact surface with the subject to be examined equal to or the same as the temperature of the ultrasonic probe relating to the prior art. This enables ultrasonic waves to be transmitted more deeply inside the subject to be examined (living body).

[Embodiment 8]

Figure 16:
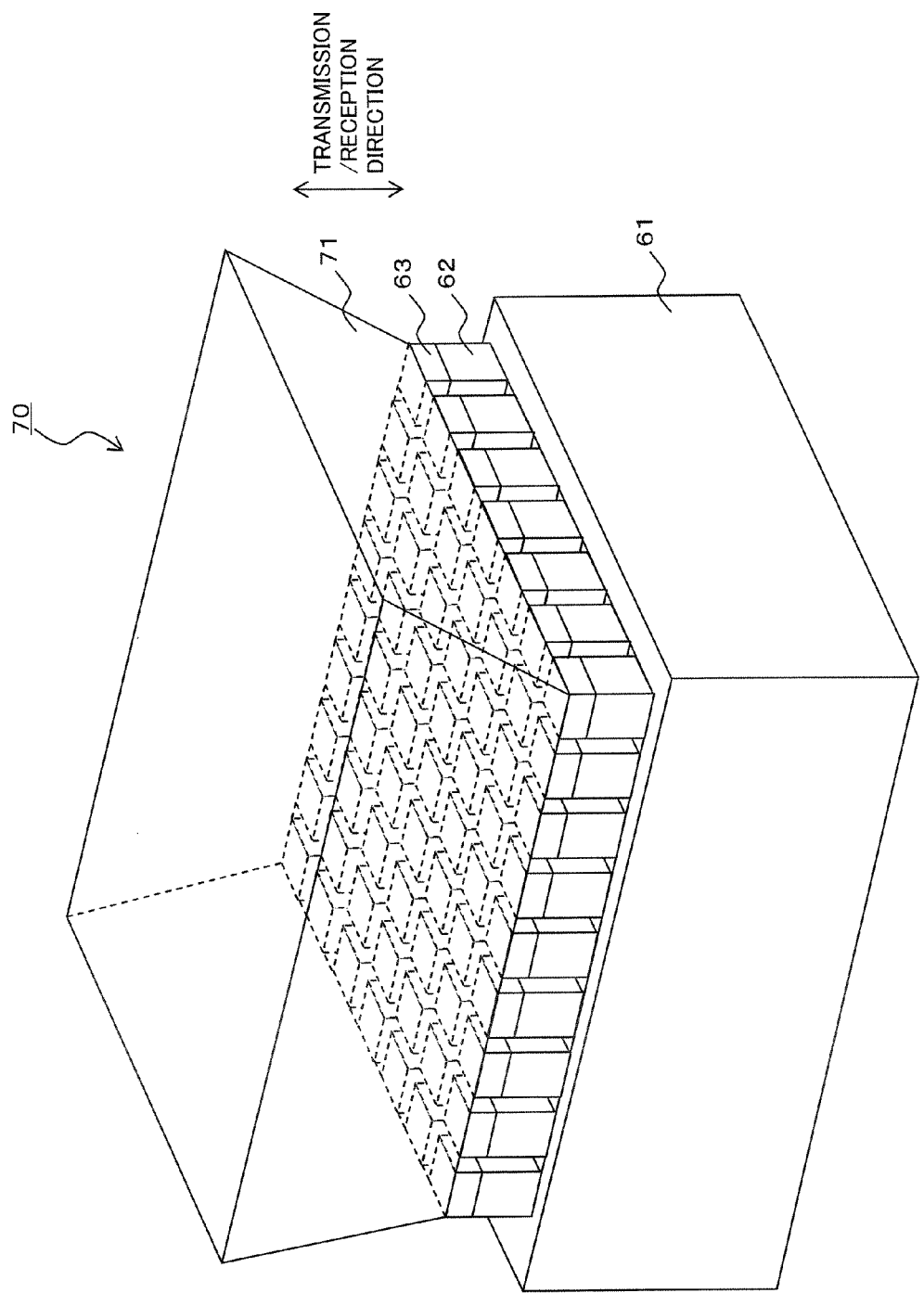
FIG. 16 represents a perspective view showing the outline constitution of the head side of the ultrasonic probe according to the eighth embodiment of the present invention.

Next, the constitution of the ultrasonic probe related to the eight embodiment of the present invention is explained in reference to FIG. 16. FIG. 16 represents a perspective view showing the outline constitution of the head side of the ultrasonic probe related to Embodiment 8 of the present invention. FIG. 16 shows the head side of the ultrasonic probe. In this Embodiment 8, similar to Embodiment 7, an explanation is provided for a so-called two-dimensional ultrasonic wave, wherein a plural of ultrasonic transducers are arranged in two-dimensionally.

The ultrasonic probe 70 related to Embodiment 8, similar to the ultrasonic probe 60 relating to Embodiment 7 described above, comprises an ultrasonic transducer section 62 in which a plural of ultrasonic transducers are arranged two-dimensionally, a backing material 61 and an acoustic matching layer 63. A low attenuation medium 71 is installed on the acoustic matching layer 63. The low attenuation medium 71 uses the same material of the low attenuation medium 6 related to Embodiment 1.

The backing material 61, ultrasonic transducer section 62, acoustic matching layer 63 and low attenuation medium 71 are housed in the probe shell (not shown in the figure). The low attenuation medium 71 is housed in the probe shell to be located at the top end (contact surface side with a subject to be examined) of the ultrasonic probe 70.

By forming the above constitution, the ultrasonic waves transmitted from the ultrasonic transducer section 62 are radiated outside of the ultrasonic probe 70 through the low attenuation medium 71. The reflection waves from the subject to be examined insolate into the ultrasonic probe 70 through the low attenuation medium 71, and thereafter, are received by the ultrasonic transducer section 62.

The low attenuation medium 71 has a shape that gradually widens toward the top end (contact surface side with the subject to be examined) of the ultrasonic probe 70. In other words, the sectional area perpendicular to the transmission/reception direction of the low attenuation medium 71 is formed such that it gradually enlarges in the direction (transmission/reception direction) away from the ultrasonic transducer section 62. The low attenuation medium 71 is formed to minimize the area of the surface (the first surface) contacting the acoustic matching layer 63, and is formed such that the sectional area expands gradually in the transmission/reception direction, and the area of the surface (surface of the top end of the ultrasonic probe 70) (the second surface) opposing the first surface is sized to be largest.

The thickness of the low attenuation medium 71 in the direction of the transmission/reception is preferably determined based on the characteristic of the sound field distribution of the ultrasonic transducer section 62, similar to Embodiment 1.

By adjusting the thickness d of the low attenuation medium 71 similar to Embodiment 1, the focus position of ultrasonic waves in the slice direction can be formed outside of the ultrasonic probe 70. In doing so, the focus position of ultrasonic waves in the slice direction can be formed inside a subject to be examined (living body), thus enabling a clear image inside the subject to be examined (living body) to be obtained.

Moreover, the top end (contact surface side with a subject to be examined) of the ultrasonic probe 70 may be convex.

(Action)

According to the ultrasonic probe 70 having the above constitution, the same action and effect of the ultrasonic probe 60 related to Embodiment 7 can be obtained. Further, according to the ultrasonic probe 70 relating to Embodiment 8, since the low attenuation medium 71 gradually widens toward the top end (contact surface with a subject to be examined) of the ultrasonic probe 70, the route of the ultrasonic waves to be transmitted and received can be contained in the low attenuation medium 71.

[Embodiment 9]

Figure 17:
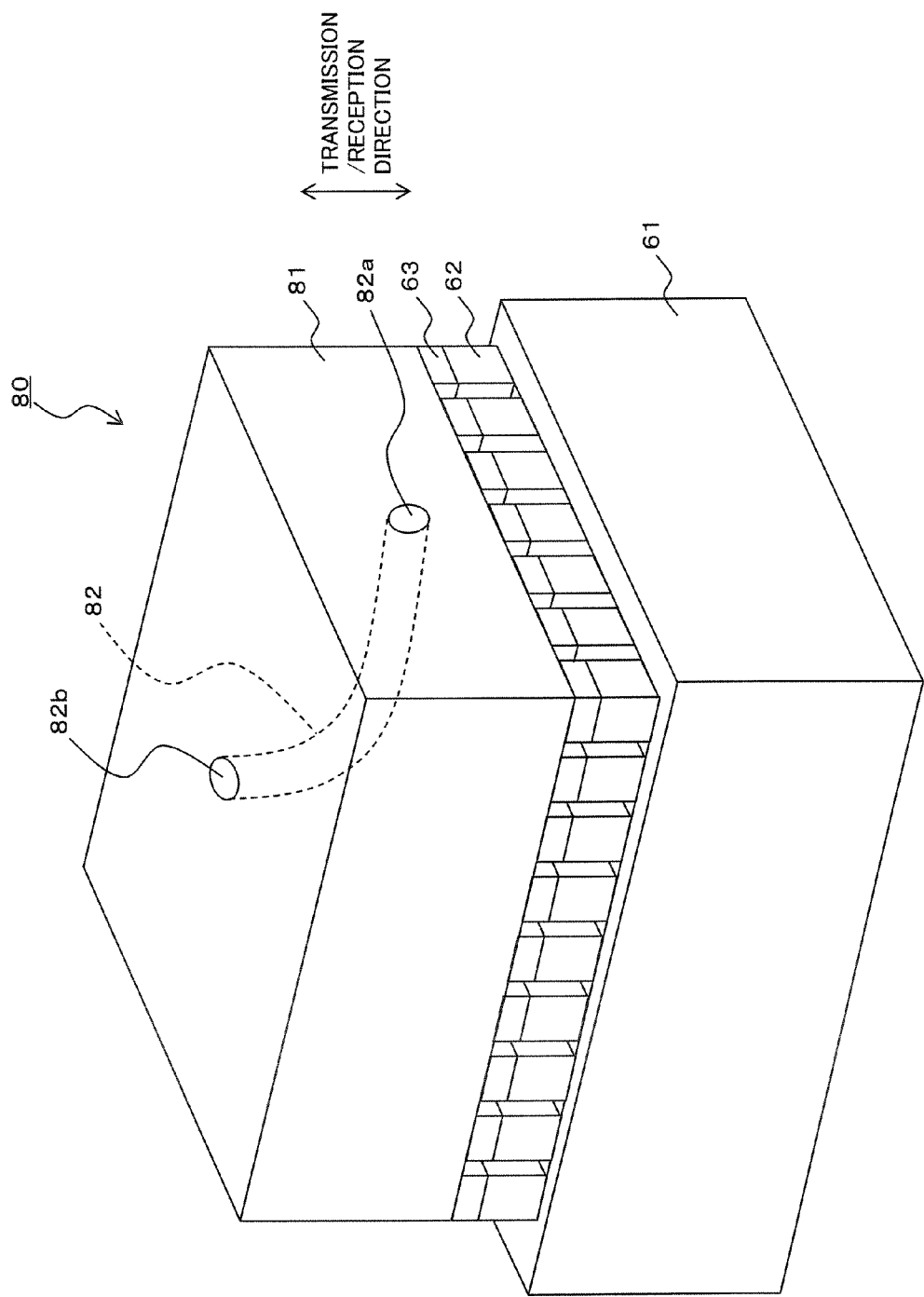
FIG. 17 represents a perspective view showing the outline constitution of the head side of the ultrasonic probe according to the ninth Embodiment of the present invention.

Next, the constitution of the ultrasonic probe related to Embodiment 9 of the present invention is explained in reference to FIG. 17. FIG. 17 represents a perspective view showing the outline constitution of the head side of the ultrasonic probe related to Embodiment 9 of the present invention. FIG. 17 shows the head side of the ultrasonic probe. In this Embodiment 9, similar to Embodiment 7, an explanation is provided for a so-called two-dimensional ultrasonic probe, wherein a plural of ultrasonic transducers are arranged in a two-dimensional configuration.

In Embodiment 9, a puncture needle guide is installed on the low attenuation medium of the ultrasonic probe 60 relating to Embodiment 7. Practically, the ultrasonic probe 80 related to Embodiment 9, similar to the ultrasonic probe 60 relating to Embodiment 7, comprises a backing material 61, an ultrasonic transducer section 62 in which a plural of ultrasonic transducers are arranged two-dimensionally, a backing material 61 and an acoustic matching layer 63. Also, a low attenuation medium 81 is installed on the acoustically matching layer 63.

Further, the backing material 61, ultrasonic transducer section 62, acoustic matching layer 63 and low attenuation medium 81 are housed in the probe shell (not shown in the figure). The low attenuation medium 81 is housed in the probe shell such that the low attenuation medium 81 is located at the top end (contact surface with the subject to be examined) of the ultrasonic probe 80.

The low attenuation medium 81 is in a cubic or rectangular parallel-piped shape. The thickness of the low attenuation medium 81 in the transmission/reception direction, similar to Embodiment 1, is preferably determined based on the characteristic of the sound field distribution of the ultrasonic transducer section 62. The thickness d of the low attenuation medium 81 is preferably greater than the distance to stabilize the sound field of ultrasonic waves.

Further, a puncture needle guide 82 is installed on the low attenuation medium 81 to guide a puncture needle to a subject to be examined (living body). The puncture needle guide 81 is cylindrical with openings at both ends to guide a puncture needle to a subject to be examined (living body) for penetration. The puncture needle guide 82 is bent at a specified curvature and installed covering from the side surface of the low attenuation medium 81 to the top end (contact surface with the subject to be examined) of the ultrasonic probe 60.

The inlet 82a (other end) of the puncture needle guide 82 is formed on the side surface of the low attenuation medium 81. On the other hand, the outlet 82b (one end) of the puncture needle guide 82 is formed on the surface of the top end of the low attenuation medium 81. In this way, the puncture needle introduced from the inlet 82a is guided outside the ultrasonic probe 80 from the outlet 82b through the puncture needle guide 82.

In Embodiment 9, the direction of the outlet 82b of the puncture needle guide 82 is perpendicular to the top end of the ultrasonic probe 80. Due to this, the puncture needle can be guided in a substantially vertical state from the outlet 82b of the puncture needle guide 82, and as a result, the puncture needle can be injected into the body surface of the subject to be examined (living body) in a substantially vertical state In Embodiment 9, although the direction of the outlet 82b of the puncture needle guide 82 is set perpendicular to the top end of the ultrasonic probe, it may be formed slanting against the top end. Moreover, the low attenuation medium 81 uses the same material as the low attenuation medium 6 in Embodiment 1. The puncture needle guide 82, similar to Embodiment 2, is formed by metal or resin.

In Embodiment 9, the puncture needle guide 82 is bent at a specified curvature, but it may also be formed in a linear state.
(Action)

According to the ultrasonic probe 80 having the above constitution, the same action and effect of the ultrasonic probe 60 related to Embodiment 7 can be obtained. Further, according to the ultrasonic probe 80 relating to Embodiment 9, a puncture needle can be identified by an ultrasonic wave image at a stage before injecting the puncture needle into a body surface, thus allowing the performance of a safe puncture needle method.

[Embodiment 10]

Figure 18:
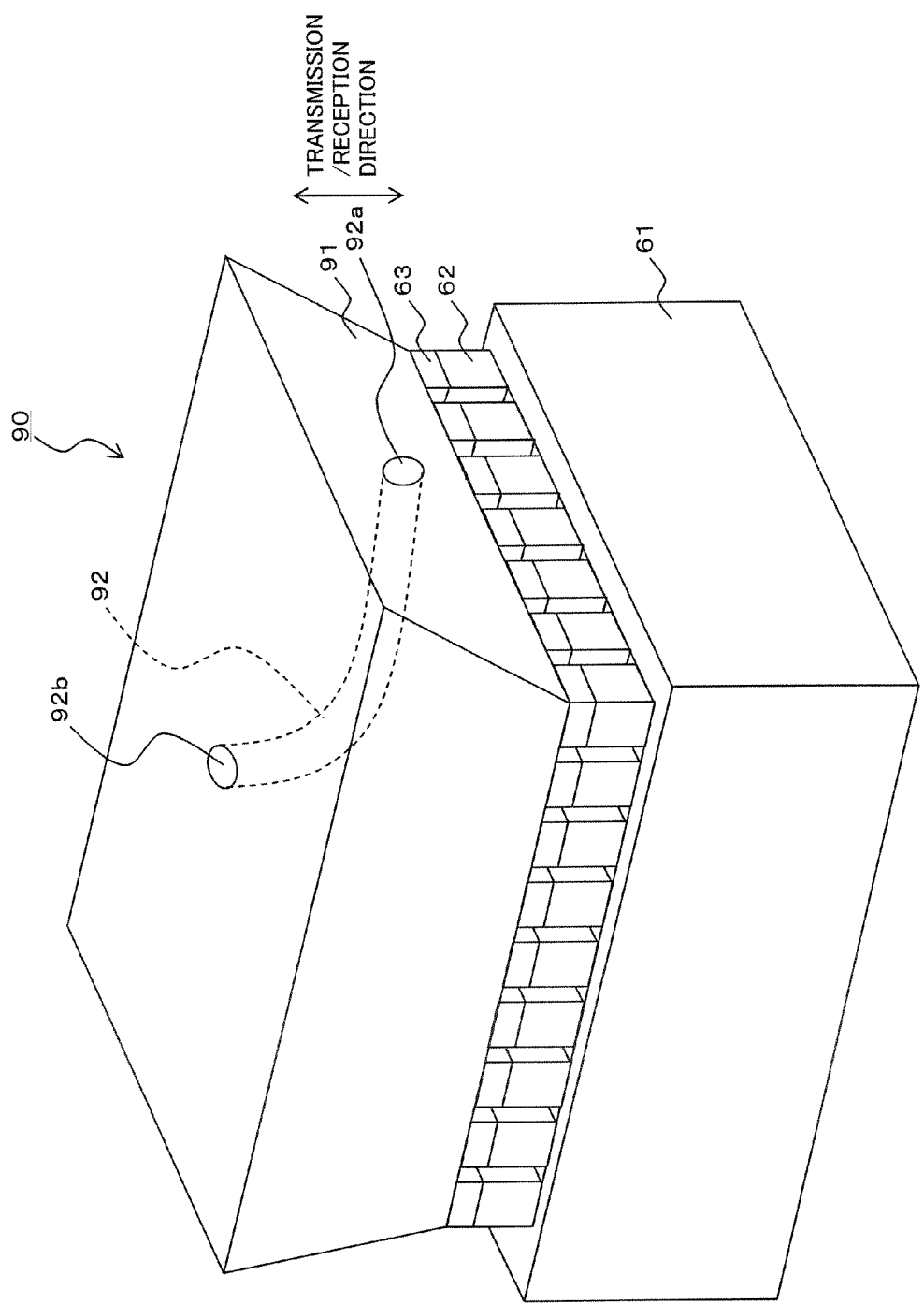
FIG. 18 represents a perspective view showing the outline constitution of the head side of the ultrasonic probe according to the tenth embodiment of the present invention.

Next, the constitution of the ultrasonic probe related to Embodiment 10 of the present invention is explained in reference to FIG. 18. FIG. 18 represents a perspective view showing the outline constitution of the head side of the ultrasonic probe related to Embodiment 10 of the present invention. FIG. 18 shows the head side of the ultrasonic probe. In this Embodiment 10, similar to Embodiment 7, an explanation is provided for a so-called two-dimensional ultrasonic wave, wherein a plural of ultrasonic transducers are arranged in a two-dimensional configuration.

In Embodiment 10, a puncture needle guide is installed on the low attenuation medium of the ultrasonic probe 70 related to Embodiment 8. Practically, the ultrasonic probe 90 relating to Embodiment 10, similar to the ultrasonic probe 70 relating to Embodiment 8, comprises a backing material 61, an ultrasonic transducer section 62 and an acoustic matching layer 63. In addition, a low attenuation medium 91 is installed on the acoustic matching layer 63. Further, the backing material 61, ultrasonic transducer section 62, acoustic matching layer 63 and low attenuation medium 91 are housed in the probe shell (not shown in the figure). At this moment, the low attenuation medium 91 is housed in the probe shell such that it is located at the top end (contact surface side with 8 the subject to be examined) of the ultrasonic probe 90.

Similarly to Embodiment 8, the low attenuation medium 91 has a shape that gradually widens toward the top end (contact surface side with a subject to be examined) of the ultrasonic probe 90. In other words, the sectional area of the low attenuation medium 91 perpendicular in the transmission/reception direction is formed such that it is gradually enlarged in the direction (transmission/reception direction) leaving the ultrasonic transducer section 62. The thickness of the low attenuation medium 91 in the transmission/reception direction is preferably determined, similar to Embodiment 1, based on the characteristic of the sound field distribution of the ultrasonic transducer section 62. The thickness d of the low attenuation medium 91 is preferably greater than the length stabilizing the sound field of ultrasonic waves.

Further, a puncture needle guide 92 is installed on the low attenuation medium 91 to guide a puncture needle to a subject to be examined (living body). The puncture needle guide 92 is cylindrical with openings at both ends to guide a puncture needle to a subject to be examined (living body) for penetration. The puncture needle guide 92 is bent at a specified curvature and installed covering from the side surface of the low attenuation medium 91 to the top end (contact surface with the subject to be examined) of the ultrasonic probe 90.

The inlet 92a (other end) of the puncture needle guide 92 is formed on the side surface of the low attenuation medium 91. On the other hand, the outlet 92b (one end) of the puncture needle guide 92 is formed on the surface of the top end of the low attenuation medium 91. In this way, the puncture needle introduced from the inlet 92a is guided outside the ultrasonic probe 90 from the outlet 92b through the puncture guide 92.

In Embodiment 10, the direction of the outlet 92b of the puncture needle guide 92 is perpendicular to the top end of the ultrasonic probe 90. Due to this, the puncture needle can be guided in a substantially vertical state from the outlet 92b of the puncture needle guide 92, and as a result, the puncture needle can be injected into the body surface of the subject to be examined (living body) in a substantially vertical state In Embodiment 10, although the direction of the outlet 92b of the puncture needle guide 92 is set perpendicular to the top end of the ultrasonic probe 90, it may be formed slanting against the top end.

Moreover, the low attenuation medium 91 uses the same material as the low attenuation medium 6 in Embodiment 1. The puncture needle guide 92, similar to Embodiment 2, is formed by metal or resin.

In Embodiment 10, the puncture needle guide 92 is bent at a specified curvature, but it may be formed in a linear state.
(Action)

According to the ultrasonic probe 90 having the above constitution, the same action and effect of the ultrasonic probe 90 related to Embodiment 8 can be obtained. Further, a puncture needle can be identified by an ultrasonic wave image at a stage before injecting the puncture needle into the body surface.

[Embodiment 11]
(Apparatus for Obtaining an Ultrasonic Image)

Figure 19:
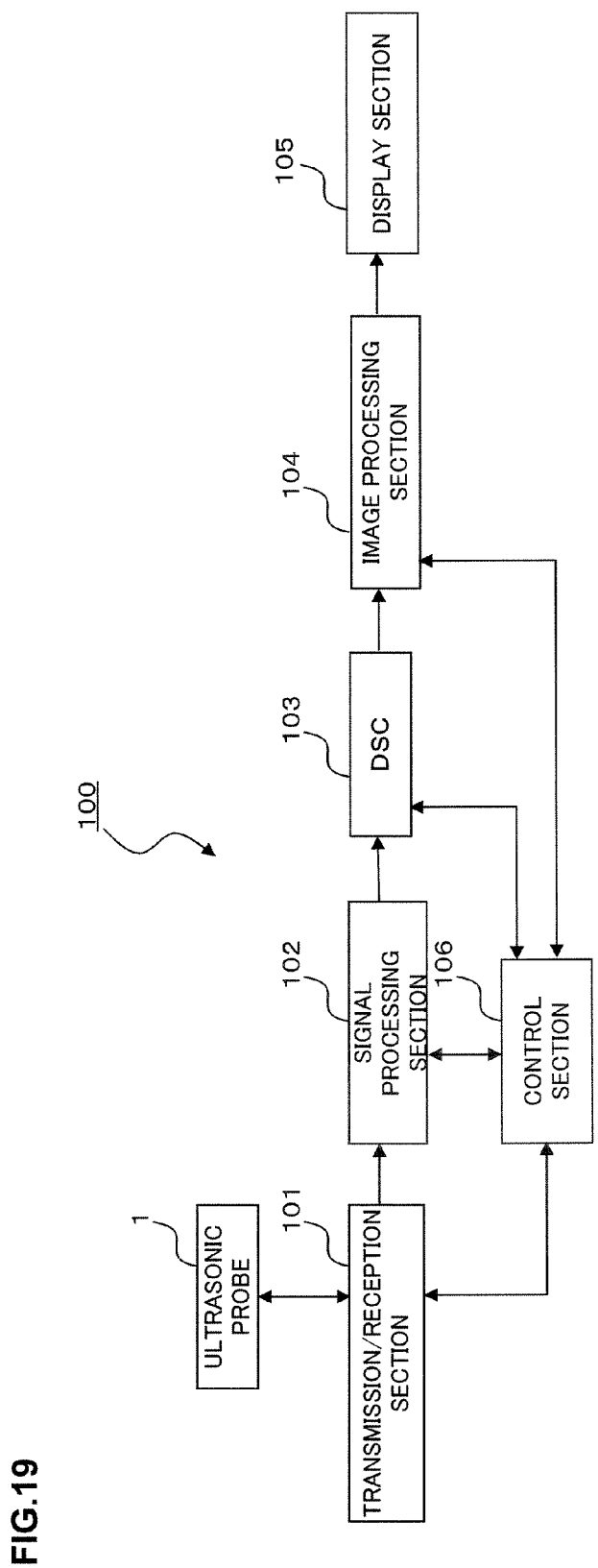
FIG. 19 represents a block chart showing the outline constitution of the head side of the ultrasonic wave image processing device according to the eleventh embodiment of the present invention.

Next, an apparatus for obtaining an ultrasonic image according to Embodiment 11 comprising the ultrasonic probe related to the above embodiment is explained in reference to FIG. 19. FIG. 19 represents a block diagram showing the outline constitution of the apparatus for obtaining an ultrasonic image according to Embodiment 11.

The apparatus for obtaining an ultrasonic image 100 according to Embodiment 11 mainly comprises an ultrasonic probe 1, a transmission/reception section 101, a signal processing section 102, a DSC 103, an image processing section 104, a display section 105, and control section 106.

In the ultrasonic probe 1, an ultrasonic probe installed with the low attenuation medium 6 described above is used. Here, the ultrasonic probe 1 according to Embodiment 1 is used; however, any of the ultrasonic probes from Embodiment 2 to Embodiment 10 may be used.

The transmission/reception section 101 comprises a transmission section and reception section from which electrical signals are supplied to the ultrasonic probe 1 to generate ultrasonic waves and the echo signals being received by the ultrasonic probe 1 are received.

The transmission section of the transmission/reception section 101 comprises a clock generation circuit, a transmission delay circuit and a pulsar circuit. The clock generation circuit is a circuit generating the clock signals to determine the transmission timing or the transmission frequency of the ultrasonic wave signal. The transmission delay circuit is a circuit to execute transmission focus by applying a delay at the transmission of ultrasonic waves. The pulsar circuit housing a pulsar in a number of individual routings (channels)

corresponding to each ultrasonic transducer generates a driving pulse at the transmission timing that is delayed to supply to each ultrasonic transducer of the ultrasonic probe 1.

The reception section of the transmission/reception section 81 comprises a preamplifier circuit (not shown in the figure), an A/D conversion circuit, and receiving delay/adder circuit. The amplifier circuit amplifies the echo signals output from each ultrasonic transducers of the ultrasonic probe 1 for each receiving channel. The A/D conversion circuit provides the A/D conversion of the echo signals amplified. The reception delay/adder circuit provides a delay time required to determine the receiving directivity of the echo signals provided with the A/D conversion for adding. By this addition, the reflection wave component in the direction of the receiving directivity is emphasized. The signal processed for adding by the transmission/reception section 101 is referred to as "RF data."

The transmission/reception section 81 preferably make the ultrasonic probe 1 transmit ultrasonic waves at a transmission output level, in accordance with the standard (EC60601-2-37), wherein the temperature of the top end 1a (contact surface with a subject to be examined) is between 30° C.~50° C.

The signal processing section 102 comprises a popular B mode processing circuit, a Doppler processing circuit, or a color mode processing circuit. The data output from the transmission/reception section 101 is specifically processed by any of the processing circuits. The B-mode processing circuit images the amplitude information on the echoes and produces B-mode raster data from the echo signals. Practically, the B-mode processing circuit executes band pass filter processing against the RF data, and then detects the envelope line of the output signals, and applies compression processing on the detected data by means of logarithmic conversion.

The Doppler circuit produces data having blood flow information by taking out the Doppler displacement frequency component and providing FFT processing.

The color mode processing circuit images the moving blood flow information to produce color raster data.

The blood flow information includes that on the velocity, dispersion, power, etc., and can be obtained as two-valued information. Practically, the color mode processing circuit comprises a phase detecting circuit, an MTI filter, an auto-correlation device, and a velocity/dispersion operator. This color mode processing circuit executes high-pass filter processing (MTI filer processing) to separate a tissue signal and a blood flow signal to obtain the blood flow information on the moving velocity, dispersion and power of blood flow at a plural of points by autocorrelation processing.

The DSC 103 (Digital Scan Converter) converts the ultrasonic raster data into data expressed by an orthogonal coordinate in order to obtain an image which can be expressed by an orthogonal coordinate (scan conversion processing). For example, if scan conversion processing is applied to the data output from the B-mode processing circuit, tomography image data is produced making the tissue shape of a subject to be examined the second-dimensional information. In addition, the DSC 103 can produce Voxel data by the re-sampling processing of tomography image data.

The image processing section 104 produces ultrasonic wave images like three-dimensional image data or MPR image data (image data of an optional section) by applying volume rendering processing or MPR (Multi Planner Reconstruction) image processing to Voxel data, for example.

The display section 105 comprising a monitor such as CRT or liquid crystal display displays an ultrasonic wave image such as a tomography image, a three-dimensional image or blood flow information on the monitor screen.

The control section 106 controls each section of the apparatus for obtaining an ultrasonic image 100. On the memory section (not shown in the figure) such as ROM, RAM, HDD, various setting conditions and control programs are stored in the memory. The control section 106 controls each section of the apparatus for obtaining an ultrasonic image 100 through the connection with each section of the apparatus for obtaining an ultrasonic image 100. The control section 106 is comprised of, for example, a CPU, and controls each section by executing the control program for the apparatus for obtaining an ultrasonic image stored in the memory section.

In addition, the apparatus for obtaining an ultrasonic image 100 is provided with an operation section (not shown in the figure) for which various settings relating to the transmission/reception conditions of ultrasonic waves are prepared. This operation section comprises a pointing device such as a joystick or trackball, switches, various buttons, and a keyboard or TCS (Touch Command Screen). The information input by this operation section is transmitted to the control section 106, where the control section 106 controls each section of the apparatus for obtaining an ultrasonic image 100 by following the information.

(Action)

According to the apparatus for obtaining an ultrasonic image 100 relating to Embodiment 11, as the ultrasonic probe relating to any embodiment from among Embodiments 1 to 10, a uniform and stable sound field can be formed near the contact surface with a living body, resulting in a clear image being obtained near the contact surface with the living body. Further, a puncture needle can be identified by an ultrasonic wave image at a stage before injecting the puncture needle into the body surface leading to a safe puncture needle method.

What is claimed is:

1. An ultrasonic probe, comprising:
   an ultrasonic transducer section having a plurality of ultrasonic transducers, wherein ultrasonic waves are transmitted to a subject to be examined and reflection waves are received from said subject to be examined;
   a low attenuation medium;
   a convergence component that converges ultrasonic waves;
   a probe shell; and
   a puncture needle guide in said low attenuation medium, said puncture needle guide being configured to guide a puncture needle into said subject to be examined in a direction perpendicular to the contact surface side, wherein
   said probe shell is configured to house said low attenuation medium, said convergence component, and said ultrasonic transducer section in order therein,
   said ultrasonic transducer section transmits the ultrasonic waves to said subject to be examined and receives the reflection waves from said subject to be examined through said convergence component and said low attenuation medium, and
   a thickness of said low attenuation medium in a transmission/reception direction is set to exceed a required distance from a probe surface so that a stable and uniform sound field distribution of the ultrasound waves is formed near the probe surface.

2. The ultrasonic probe according to claim 1, wherein:
   said ultrasonic transducer section, having said plurality of ultrasonic transducers provided in a row in a scanning direction, transmits ultrasonic waves to said subject to be examined and receives the reflection waves from said subject to be examined, and said convergence component converges said ultrasonic waves to be transmitted and received in a slice direction perpendicular to both said scanning direction and to a direction of transmitting said ultrasonic waves.

3. The ultrasonic probe according to claim 2, wherein:
an area of a first surface of the low attenuation medium facing said convergence component is larger than an area of a second surface of the low attenuation medium located opposing said first surface.

4. The ultrasonic probe according to claim 2, wherein:
a width of said low attenuation medium in said slice direction gradually narrows toward a tip of the low attenuation medium.

5. The ultrasonic probe according to claim 1, wherein:
a center of a tip of the low attenuation medium substantially equals a position of a focus of said ultrasonic waves.

6. The ultrasonic probe according to claim 1, wherein:
said low attenuation medium is tapered toward a tip of the low attenuation medium.

7. The ultrasonic probe according to claim 1, wherein:
an attenuation rate of ultrasonic waves of said low attenuation medium counts at 0.2 [dB/mm·MHz] or less.

8. The ultrasonic probe according to claim 1, wherein:
said low attenuation medium is a solid body.

9. The ultrasonic probe according to claim 1, wherein:
said low attenuation medium comprises resin.

10. The ultrasonic probe according to claim 1, wherein:
the puncture needle guide is bent in a curve to guide the puncture needle inside the subject to be examined in a direction perpendicular to a tip of the low attenuation medium.

11. The ultrasonic probe according to claim 1, wherein:
said ultrasonic transducer section, comprising said plurality of ultrasonic transducers provided in a row in a scanning direction, transmits ultrasonic waves to said subject to be examined and receives the reflection waves from said subject to be examined,
said convergence component converges said transmitted and received ultrasonic waves in a slice direction perpendicular to both said scanning direction and to a direction of transmitting said ultrasonic waves, and
said puncture needle guide is configured to guide said puncture needle along a plane parallel to a plane including said direction of transmitting said ultrasonic waves and said scanning direction.

12. The ultrasonic probe according to claim 11, wherein:
said puncture needle guide is configured to guide said puncture needle in a direction perpendicular to a tip of the low attenuation medium.

13. The ultrasonic probe according to claim 11, wherein:
said puncture needle guide is configured to guide the puncture needle to a substantially central position of a tip of the low attenuation medium in a direction perpendicular to the tip of the low attenuation medium.

14. The ultrasonic probe according to claim 11, wherein:
a width of said low attenuation medium in the scanning direction becomes gradually wider towards a tip of the low attenuation medium from the side with which said ultrasonic transducer section is provided.

15. The ultrasonic probe according to claim 11, wherein:
said low attenuation medium is convex in shape at a tip of the low attenuation medium.

16. The ultrasonic probe according to claim 1, wherein:
said puncture needle guide is configured to guide said puncture needle along a plane parallel to the plane including a direction of transmitting said ultrasonic waves and a scanning direction of the ultrasonic waves.

17. The ultrasonic probe according to claim 1, wherein:
said puncture needle guide is bent to guide the puncture needle towards a tip of the low attenuation medium in a direction perpendicular to the tip of the low attenuation medium, the puncture needle being inserted from a side different from said tip of the low attenuation medium.

18. The ultrasonic probe according to claim 1, further comprising:
a coupling part comprising said puncture needle guide, wherein said low attenuation medium includes a concave part,
said coupling part being coupled with said concave part of said low attenuation medium.

19. An ultrasonic probe, comprising:
an ultrasonic transducer section, having a plurality of ultrasonic transducers provided in a row in a scanning direction, that transmits ultrasonic waves to a subject to be examined and receives the reflection waves from said subject to be examined;
a convergence component for converging the ultrasonic waves to be transmitted and received in a direction perpendicular to both said scanning direction and to a direction of transmitting said ultrasonic waves;
a low attenuation medium in solid state;
a probe shell; and
a puncture needle guide in said low attenuation medium to guide the puncture needle into said subject to be examined in a direction perpendicular to the contact surface side, wherein
said probe shell is configured to house said low attenuation medium, said convergence component, and said ultrasonic transducer section in order therein;
said low attenuation medium is tapered toward a tip on an opposite side from the convergence component;
said ultrasonic transducer section transmits the ultrasonic waves to said subject to be examined and receives the reflection waves from said subject to be examined through said convergence component and said low attenuation medium;
a thickness of the low attenuation medium in a transmission/reception direction is set to exceed a required distance from a probe surface so that a stable and uniform sound field distribution of the ultrasound waves is formed near the probe surface; and
a position of the contact surface side contacting said subject to be examined is substantially equal to the position of a focus of said ultrasonic waves.

20. The ultrasonic probe according to claim 19 wherein:
the puncture needle guide is configured to guide said puncture needle along a plane parallel to a plane including the direction of transmitting said ultrasonic waves and said scanning direction.

21. An apparatus for obtaining an ultrasonic image, comprising:
an ultrasonic transducer section, including a plurality of ultrasonic transducers, that transmits ultrasonic waves to a subject to be examined and receives reflection waves from said subject to be examined;
a low attenuation medium;
a convergence component that converges the ultrasonic waves;
a probe shell;

a puncture needle guide in said low attenuation medium to guide a puncture needle into said subject to be examined in a direction perpendicular to the contact surface side; and an image data generator, wherein said probe shell is configured to house said low attenuation medium, said convergence component, and said ultrasonic transducer section in order therein;

said ultrasonic transducer section transmits the ultrasonic waves to said subject to be examined through said convergence component and said low attenuation medium and receives the reflection waves from said subject to be examined;

a thickness of the low attenuation medium in a transmission/reception direction is set to exceed a required distance from a probe surface so that a stable and uniform sound field distribution of the ultrasound waves is formed near the probe surface; and said image data generator is configured to generate ultrasonic wave image data according to the reflection wave received by said ultrasonic transducer section.

22. The apparatus for obtaining an ultrasonic image according to claim 21, wherein the puncture needle guide is configured to guide the puncture needle along a plane parallel to the plane including a direction of transmitting said ultrasonic waves and a scanning direction of the ultrasonic waves.

23. The apparatus for obtaining an ultrasonic image according to claim 21, wherein:

said ultrasonic transducer section is configured to transmit the ultrasonic waves so that a temperature at the contact surface side contacting said subject to be examined is from 30° C. to 50° C.

* * * * *